United States Patent
Kawakami et al.

(10) Patent No.: US 8,188,971 B2
(45) Date of Patent: May 29, 2012

(54) MEDICAL IMAGE INTERPRETING APPARATUS AND CURSOR-MOVING METHOD

(75) Inventors: Jun Kawakami, Otawara (JP); Kenichi Niwa, Otawara (JP); Maki Minakuchi, Otawara (JP); Takashi Kondo, Nasushiobara (JP); Takashi Masuzawa, Otawara (JP)

(73) Assignees: Kabushiki Kaisha Toshiva, Tokyo (JP); Toshiba Medical Systems Corporation, Otawara-shi (JP)

( * ) Notice: Subject to any disclaimer, the term of this patent is extended or adjusted under 35 U.S.C. 154(b) by 1337 days.

(21) Appl. No.: 11/685,895

(22) Filed: Mar. 14, 2007

(65) Prior Publication Data

US 2007/0219651 A1    Sep. 20, 2007

(30) Foreign Application Priority Data

Mar. 15, 2006    (JP) ................... 2006-071388

(51) Int. Cl.
   *G06F 3/02* (2006.01)
(52) U.S. Cl. .......... 345/157; 345/168; 345/172; 700/83; 715/781; 715/856
(58) Field of Classification Search .......... 345/156–184; 700/83; 715/856, 781
See application file for complete search history.

(56) References Cited

U.S. PATENT DOCUMENTS

| | | | | |
|---|---|---|---|---|
| 4,987,411 A | * | 1/1991 | Ishigami | 345/159 |
| 5,367,631 A | | 11/1994 | Levy | |
| 5,414,811 A | * | 5/1995 | Parulski et al. | 345/501 |
| 5,585,821 A | * | 12/1996 | Ishikura et al. | 715/856 |
| 6,901,277 B2 | * | 5/2005 | Kaufman et al. | 600/407 |
| 2004/0012562 A1 | * | 1/2004 | Aymeric | 345/157 |
| 2005/0012723 A1 | * | 1/2005 | Pallakoff | 345/173 |
| 2006/0059012 A1 | * | 3/2006 | Thompson | 705/2 |

FOREIGN PATENT DOCUMENTS

| | | |
|---|---|---|
| JP | 4-246716 | 9/1992 |
| JP | 6-12185 | 1/1994 |
| JP | 8-335138 | 12/1996 |
| JP | 9-114594 | 5/1997 |
| JP | 9-288544 | 11/1997 |
| JP | 10-222307 | 8/1998 |
| JP | 2000-89891 | 3/2000 |
| JP | 2001-67179 | 3/2001 |
| JP | 2003-241884 | 8/2003 |
| JP | 2003-330594 | 11/2003 |
| JP | 2005-31719 | 2/2005 |
| WO | WO 2006025653 A1 * | 3/2006 |

* cited by examiner

*Primary Examiner* — Lun-Yi Lao
*Assistant Examiner* — Sosina Abebe
(74) *Attorney, Agent, or Firm* — Oblon, Spivak, McClelland, Maier & Neustadt, L.L.P.

(57) ABSTRACT

In the medical image interpreting apparatus having a pointing device for moving a cursor, medical image, interpretation report, and cursor are displayed on a display screen, and initial movement information and information on the destination of movement of the cursor are linked and stored, via the pointing device when the cursor begins to move, said initial movement information relevant to the initial movement is retrieved to obtain the linked information on the destination of movement and the cursor is moved to the destination of movement indicated in the obtained information on the destination of movement. Due to this, just by slightly moving the cursor, the cursor jumps to the desired destination of movement, therefore, it becomes possible to omit an operation of the pointing device in between. Due to this, the operation load of the pointing device is reduced, thus preventing an operator's thought in creating an interpretation report from being destructed, and the enhancement in interpreting efficiency and the reduction of interpretation mistakes are achieved.

5 Claims, 25 Drawing Sheets

FIG. 2
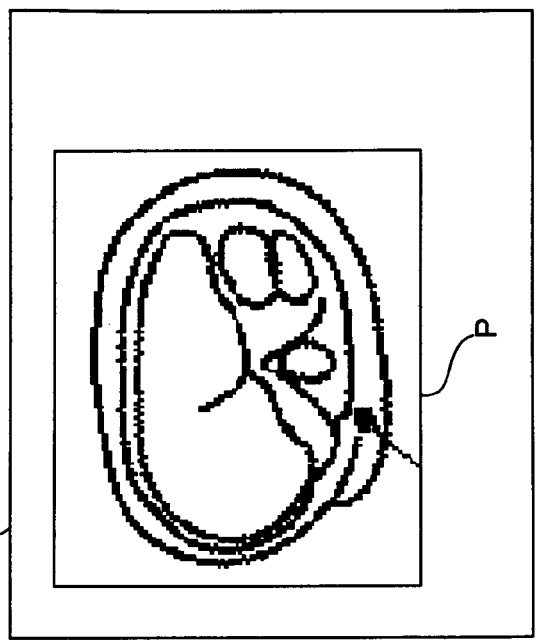
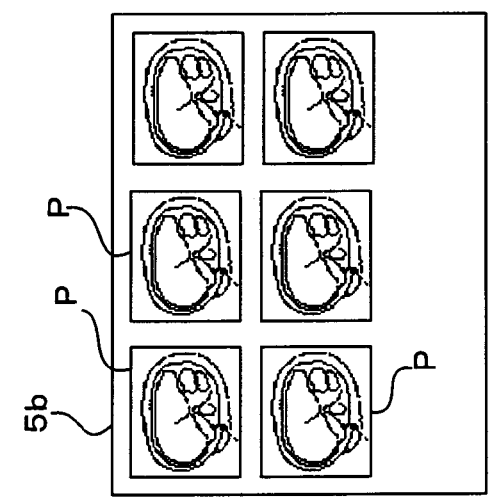

FIG. 7

| INITIAL MOVEMENT INFORMATION ||
|---|---|
| INFORMATION ON THE ORIGIN OF MOVEMENT | INITIAL MOVEMENT DIRECTION INFORMATION |
| C8 | Dir8 |

FIG. 8

| INFORMATION ON THE DESTINATION OF MOVEMENT ||
|---|---|
| X1 | Y1 |
| 3089 | 502 |

FIG. 9

| PREDICTION INFORMATION ||||||
|---|---|---|---|---|
| INITIAL MOVEMENT INFORMATION || INFORMATION ON THE DESTINATION OF MOVEMENT || NUMBER OF LEARNING TIMES |
| INFORMATION ON THE ORIGIN OF MOVEMENT | INITIAL MOVEMENT DIRECTION INFORMATION | X2 | Y2 | |
| C8 | Dir8 | 3100 | 500 | 8 |

FIG. 10

| PREDICTION INFORMATION ||||||
|---|---|---|---|---|
| INITIAL MOVEMENT INFORMATION || INFORMATION ON THE DESTINATION OF MOVEMENT || NUMBER OF LEARNING TIMES |
| INFORMATION ON THE ORIGIN OF MOVEMENT | INITIAL MOVEMENT DIRECTION INFORMATION | X2 | Y2 | |
| C8 | Dir8 | 3098 | 500 | 9 |

FIG.13

| INITIAL MOVEMENT INFORMATION ||
|---|---|
| INFORMATION ON THE ORIGIN OF MOVEMENT | INITIAL MOVEMENT DIRECTION INFORMATION |
| C8 | Dir8 |

FIG. 14

| PREDICTION INFORMATION ||||| 
|---|---|---|---|---|
| INITIAL MOVEMENT INFORMATION || INFORMATION ON THE DESTINATION OF MOVEMENT || NUMBER OF LEARNING TIMES |
| INFORMATION ON THE ORIGIN OF MOVEMENT | INITIAL MOVEMENT DIRECTION INFORMATION | X2 | Y2 | |
| C8 | Dir8 | 3098 | 500 | 9 |

FIG. 18

| INTERPRETATION REPORT |
|---|
| ................................................................<br><br>=HYPERLINK("¥¥IMAGE SERVER¥IMAGE FOLDER¥TARO YAMADA¥MEDICAL IMAGE P.jpg","TUMORS IN BOTH LOBES OF THE LIVER")<br><br>................................................................<br><br>................................................................<br><br>................................................................<br><br>........... |

FIG. 21

| A SET OF JUMP AREA INFORMATION ||||
|---|---|---|---|
| JUMP AREA INFORMATION || JUMP AREA INFORMATION ||
| COORDINATES' RANGE INFORMATION | CENTER COORDINATE INFORMATION | COORDINATES' RANGE INFORMATION | CENTER COORDINATE INFORMATION |

FIG. 23

| JUMP AREA INFORMATION | | |
|---|---|---|
| CORRESPONDING BUTTON INFORMATION | COORDINATES' RANGE INFORMATION | CENTER COORDINATE INFORMATION |

| JUMP AREA INFORMATION | | |
|---|---|---|
| CORRESPONDING BUTTON INFORMATION | COORDINATES' RANGE INFORMATION | CENTER COORDINATE INFORMATION |

| JUMP AREA INFORMATION | | |
|---|---|---|
| CORRESPONDING BUTTON INFORMATION | COORDINATES' RANGE INFORMATION | CENTER COORDINATE INFORMATION |

FIG. 26A

| JUMP AREA INFORMATION ||||
|---|---|---|---|
| ENTRY JUMP AREA INFORMATION || EXIT JUMP AREA INFORMATION ||
| COORDINATES' RANGE INFORMATION | CENTER COORDINATE INFORMATION | | |

FIG. 26B

| JUMP AREA INFORMATION ||||
|---|---|---|---|
| ENTRY JUMP AREA INFORMATION || EXIT JUMP AREA INFORMATION ||
| COORDINATES' RANGE INFORMATION | CENTER COORDINATE INFORMATION | COORDINATES' RANGE INFORMATION | CENTER COORDINATE INFORMATION |

FIG. 30

| PREDICTION INFORMATION | | | | |
|---|---|---|---|---|
| INITIAL MOVEMENT INFORMATION | | INFORMATION ON THE DESTINATION OF MOVEMENT | | NUMBER OF LEARNING TIMES |
| INFORMATION ON THE ORIGIN OF MOVEMENT | INITIAL MOVEMENT DIRECTION INFORMATION | X2 | Y2 | |
| B8 | Dir5 | 800 | 300 | 8 |
| PRESCRIBED PROGRAM | | | | |
| HYPERLINK PROCESS | | | | |
| PRESCRIBED DISTANCE INFORMATION D | | | | |
| 100 | | | | |

MEDICAL IMAGE INTERPRETING APPARATUS AND CURSOR-MOVING METHOD

BACKGROUND OF THE INVENTION

1. Field of the Invention

The present invention relates to a technology for moving a cursor when an interpretation report is being created.

2. Description of the Related Art

Nowadays, accompanied by upgraded medical acts, the diagnoses of patients are divided into different levels, and a specialist is involved at each level. In general, an image diagnosis is conducted procedurally as follows: image diagnosis request, image collection, interpretation, and determination of the treatment policy.

For an image diagnosis request, a request form is submitted to a radiography department from the department requesting an examination such as the department of internal medicine. The request form includes the following items: the ID number of the patient, the patient's name, date of birth, sex, name of the department requesting the examination, name of the doctor requesting the examination, modality of the examination, subject of the examination, method of examination, purpose of the examination, and clinical information. In image collection, an examining technologist collects images as per the content of the request form. In the interpretation, an interpreting doctor interprets the collected images and summarizes the result in an interpretation report. The interpretation report includes information such as the findings of the interpreting doctor and his conclusions. To determine the treatment policy, a doctor in charge determines the treatment policy based on the interpretation report.

A medical image interpreting apparatus is used for interpretation and to electronically create an interpretation report (e.g., cf. "Japanese Unexamined Patent Application Publication No. 2005-31719"). A medical image obtained as part of the image collection is obtained and displayed on a monitor, and at the same time, a sheet of the interpretation report is displayed. The interpreting doctor inputs the necessary items on the sheet of the interpretation report.

The medical image interpreting apparatus is composed of a computer having a plurality of monitors, and a keyboard or a pointing device that is used as for a man-machine interface. The plurality of monitors have a common two-dimensional coordinate plane and are composed of a monitor for displaying an interpretation report, a monitor for a thumbnail-display of a medical image, and a monitor for an enlarged display of one medical image. A mouse cursor is displayed on the common two-dimensional coordinate plane. The interpreting doctor moves the mouse cursor to the desired position on a desired monitor for interpretation and creation of the report while performing the necessary work at that position.

For example, by moving a mouse cursor onto a medical image that displays as thumbnails, one medical image is selected for the enlarged display on a separate monitor. The mouse cursor is moved onto the medical image that has been enlarged and displayed for interpretation while adjusting the contrast, enlarging/reducing the size, and so forth. The mouse cursor is then returned to the interpretation report for writing the findings in the interpretation report. By moving the mouse cursor again to the medical image that has been enlarged and displayed, the medical image is dragged and dropped to a character string on the interpretation report to set a hyperlink. The interpreting doctor repeats the routine several times for interpretation and creation of the interpretation report while reciprocally moving the mouse cursor a number of times onto the interpretation report, the thumbnailed medical images, and the medical image that has been enlarged and displayed.

The burden of moving the mouse cursor can disrupt the interpretation and creation of the interpretation report. Consequently, concern about a possible deterioration of the interpreting efficiency or interpretation mistakes is now being addressed. Particularly, for the monitor that displays a medical image, it takes more effort to move the mouse cursor, because a monitor capable of hi-resolution display is often used.

SUMMARY OF THE INVENTION

The purpose of the present invention is to provide technology that reduces the burden of moving a cursor in the task of interpreting a medical image.

The first embodiment of the present invention relates to cursor movements of a medical image interpreting apparatus that has a pointing device for moving the cursor and supports the interpretation and creation of the interpretation report of a medical image. The initial movement of the cursor and its destination are mapped and stored in the medical image interpreting apparatus to be associated together. The medical image, the interpretation report, and the cursor are displayed on a display screen. Manipulated by the pointing device, once the cursor begins to move, information on the initial movement relevant to the initial movement is retrieved, and the associated destination of movement is obtained. When information on the destination of movement is obtained, the cursor is moved to the destination of movement indicated in the information obtained of the destination of movement.

According to the first embodiment of the present invention, as the cursor jumps to a desired destination of movement by slightly moving the cursor, it becomes possible to omit the intermediate operation of the pointing device. Thus, the burden of operating the pointing device is reduced, thereby preventing an operator's thoughts from being disrupted in creating an interpretation report, resulting in an enhancement of interpretation efficiency and a reduction in interpretation mistakes.

The initial movement information includes information on the origin of movement and the initial movement direction, whereby the information on the origin of movement may be regional information on the display screen divided into a plurality of regions. Furthermore, the region to which the origin of movement of the cursor belongs may be determined when the cursor begins to move via the pointing device. Accordingly, even if the origin of movement and the initial movement direction do not completely match according to the coordinating unit, the destination of movement becomes predictable, so the amount of the initial movement information and the information on the destination of movement to be stored is reduced, thereby easing the retrieving load, and the cursor may swiftly be jump-displayed.

Moreover, by detecting a specific operation for instructing a learning mode, from the status of movement of the cursor via the pointing device after the specific operation is detected, the initial movement information and the information on the destination of movement may be obtained and stored in the storage part. Thus, the initial movement and destination of movement of the cursor may be learned, and it becomes possible to enhance certainty of the predictable destination of movement.

Furthermore, the second embodiment of the present invention relates to the cursor's movements of a medical image interpreting apparatus that has a pointing device for moving a cursor and supports interpretation and creation of the interpretation report for a medical image. In the medical image interpreting apparatus, a work area associated with a prescribed process is preliminarily stored. Moreover, the medical image, the work area, the interpretation report, and the cursor are displayed on a display screen. When an instructed work incorporation destination is stored and when the selected data is dragged and dropped in the work area, the prescribed process with respect to the selected data is incorporated into the work incorporation destination.

According to the second embodiment, as the work incorporation destination and the data to be processed are both selected for the prescribed process, the reciprocating movement of the cursor between the work incorporation destination and the data is no longer required, so it becomes possible to reduce the operational volume of the pointing device. Therefore, the operational load of the pointing device is reduced, resulting in an enhancement in interpretation efficiency and a reduction in interpretation mistakes without disrupting an operator's thoughts in creating an interpretation report.

Furthermore, the third embodiment of the present invention relates to cursor movements of a medical image interpreting apparatus that has a pointing device for moving a cursor and supports interpretation and creation of the interpretation report of a medical image. In the medical image interpreting apparatus, the medical image, the interpretation report, the cursor, and a set of areas are displayed on a display screen. Then, movement of the cursor with respect to one of the areas is determined, and once it is determined that the cursor has moved to one of the areas, the cursor is moved into the other of the areas.

According to the third embodiment of the present invention, simply by moving the cursor into one area, the cursor appears in the other distant area. The intermediate pointing device operation may be omitted. Thus, the operational load of the pointing device is reduced, thereby preventing an operator's thoughts in creating an interpretation report from being disrupted, resulting in an enhancement of interpretation efficiency and a reduction in interpretation mistakes.

In the third embodiment of the present invention, the medical image interpreting apparatus has a plurality of input buttons, and by associating the buttons with each the area, when it is determined that the cursor has moved into one of the areas, and any one of the buttons is pressed, the cursor may be moved into the area corresponding to the pressed button.

Moreover, in the third embodiment of the present invention, by displaying one of the set of areas, once a region is designated on the display screen, and by displaying the designated region as the other of the set of areas, a determination may be made for the cursor to make a drag-movement to one of the areas while maintaining the designated state of the medical image, and once it is determined that the drag-movement has been made, the cursor may be moved into the other area while maintaining the designated state.

BRIEF DESCRIPTION OF THE DRAWINGS

FIG. 2 shows a screen to be displayed on a monitor.

FIG. 7 is one example showing stored initial movement information accompanying the initial movement of a cursor.

FIG. 8 shows an example of stored information on the destination of movement accompanying the stopped movement of a cursor.

FIG. 9 shows prediction information.

FIG. 10 shows prediction information of the movement of a cursor incorporated in the learning mode.

FIG. 12 shows monitor displays in the learning incorporation mode.

FIG. 13 is an example showing the stored initial movement information accompanying the initial movement of a cursor.

FIG. 14 is an example showing prediction information.

FIG. 17 shows monitor displays in the incorporated movement mode.

FIG. 18 shows a work incorporation destination whereby a hyperlink process associated with a work area is incorporated.

FIG. 20 shows monitor displays in jump movement mode.

FIG. 21 shows jump area information.

FIG. 23 shows jump area information related to the present modification example.

FIG. 24 shows monitor displays in jump movement mode related to the modification example.

FIG. 26 shows jump area information related to the present modification example.

FIG. 27 shows monitor displays in jump movement mode related to the modification example.

FIG. 30 shows prediction information related to the second modification example of predicted jump movement.

DETAILED DESCRIPTION OF THE EMBODIMENT

Hereinafter, appropriate embodiments of a medical image interpreting apparatus related to the present invention are described in detail with reference to figures.

Figure 1:
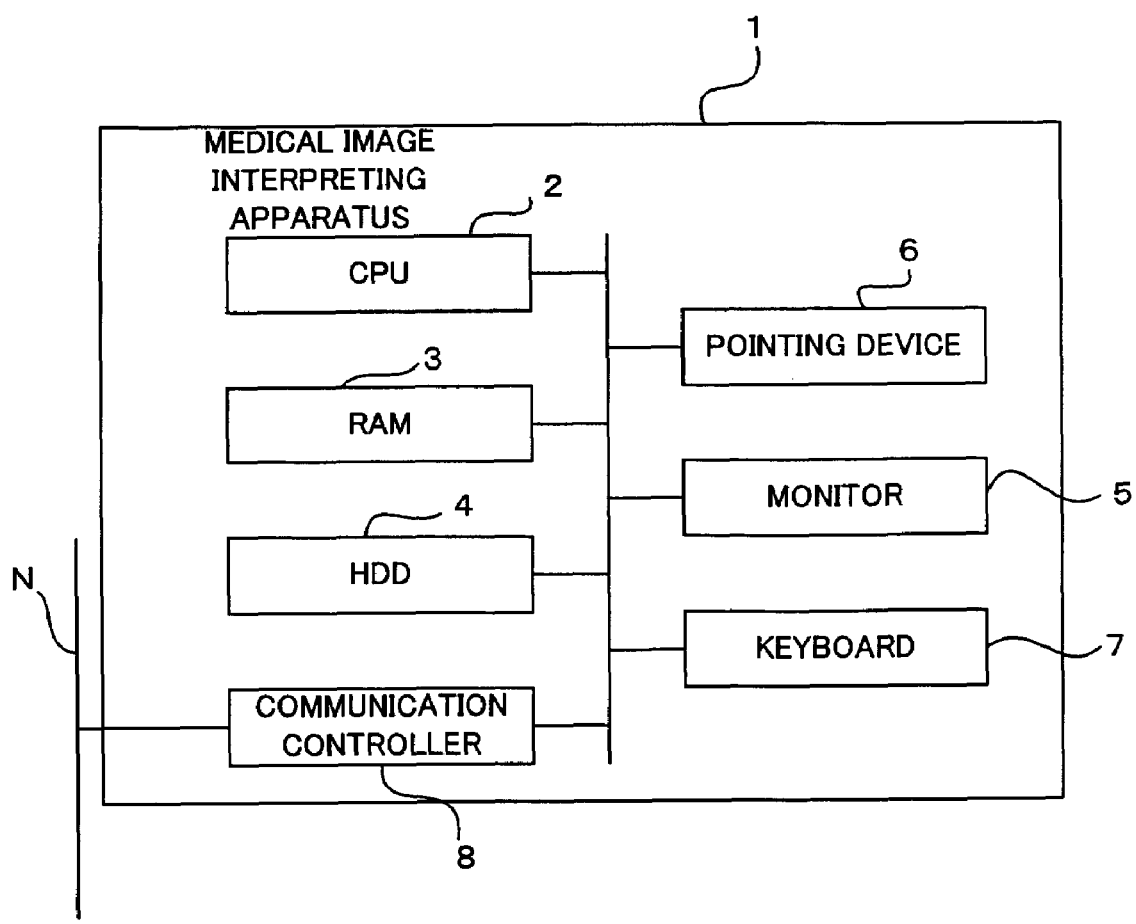
FIG. 1 shows components of a medical image interpreting apparatus related to the present embodiment.

FIG. 1 is a block diagram showing components of a medical image interpreting apparatus related to the present embodiment. The medical image interpreting apparatus 1 comprises a computer internally provided with an arithmetic control part (CPU: Central Processing Unit) 2, a main storage part (RAM: Random Access Memory) 3, an external storage part (HDD: Hard Disk Drive) 4, and a communication controller 8, that are connected by a common line and are capable of mutual data input/output. Furthermore, as a man-made machine interface, a monitor 5, a pointing device 6, and a keyboard 7 are connected through an input/output controller that is not illustrated.

The arithmetic control part 2 interprets and executes programs for the calculation of data and control of devices. The main storage part 3 is a work area of the arithmetic control part 2 for rolling out programs and for temporarily storing the calculated result or the data that has been read out. The external storage part 4 stores an OS (operating system) and an interpretation program. The interpretation program includes programs such as: obtaining and displaying medical images; creating an interpretation report according to the input of an operator; and a mouse cursor movement.

The communication controller 8 is connected to a network N for controlling data communication through the network N. The network N is an electronic communication line capable of transmitting electronic data, whereby telephone line network, ISDN, FDDI, tie line, mobile communication network, communication satellite line, CATV, LAN, etc., or a combination of these, for example, are to be adopted.

To the network N, an image server that has not been illustrated is connected. In the image server, medical images have been saved. Data communication control of the communication controller 8 allows the medical image interpreting apparatus 1 to obtain medical images from the image server through the network N. For the data communication control of communication controller 8, WWW (World Wide Web), TCP/IP protocol, or DICOM (Digital Imaging and Communications in Medicine) protocol and the like, for example, are to be adopted.

The monitor 5 constitutes a LCD display or a CRT display, and displays an interpretation report that is being created, a medical image, and a mouse cursor, according to the graphic data output from the arithmetic control part 2. A plurality of monitors 5 are connected to the medical image interpreting apparatus 1 for displaying an interpretation report or medical images.

The pointing device 6 is a device for moving the mouse cursor displayed on the monitor 5. Therein, the X-axis roller and the Y-axis roller are provided and the movement distance in the X-axis direction and in the Y-axis direction from each rotational quantum is obtained, coded as the coordinates' position data, and output to the arithmetic control part 2. The arithmetic control part 2 controls the display of the mouse cursor to the coordinates' position over the monitor 5 every time that the coordinates' position data is entered.

Furthermore, while the mouse cursor is operated by the pointing device 6 known as a mouse, the pointing device 6 may be an apparatus moving a cursor such as a trackball and a touchpad instead of a mouse. Thus, these cursors operated by the pointing device 6 other than a mouse are also referred to as a mouse cursor for the sake of convenience in the following embodiments.

FIG. 2 shows screens to be displayed on the monitor 5 of the medical image interpreting apparatus 1. As shown in FIG. 2, three monitors 5a, 5b, and 5c, for example, are connected to the medical image interpreting apparatus 1. On the monitor 5a, an interpretation report R is displayed. On the monitor 5b, as an example, the same series of medical images P are displayed. On the monitor 5c, among the same series of medical images P, a particularly interesting medical image P is enlarged and displayed.

Furthermore, on the monitors 5a, 5b, and 5c, the mouse cursor C is being displayed at the coordinates' position that has been output from the pointing device 6. The monitors 5a, 5b, and 5c have a common two-dimensional coordinate plane on which any range in the coordinate plane is displayed. As for the interpretation report R or the medical image P, the display position is initially set to match the range to be displayed. The mouse cursor C moves among 5a, 5b, and 5c in accordance with the coordinates' position data and is similarly displayed on any one of them.

In this display state, the medical image interpreting apparatus 1 of the present embodiment generates interruption processing according to the input operation using the pointing device 6 or the keyboard 7. Due to the interruption processing, the arithmetic control part 2 rolls out the mouse cursor movement program in the main storage part 3 according to the input operation for the interpretation and the execution.

That is, in accordance with the input operation, the arithmetic control part 2 prompts the mouse cursor C to a normal movement, a predicted jump movement, a prescribed spot jump movement, or an incorporated movement. In the normal movement of the mouse cursor C, whenever there is continuous output from the pointing device 6 to the coordinates' position data, the mouse cursor C is subjected to continuous movement display.

In the predicted jump movement of the mouse cursor C, the mouse cursor C is subjected to jump-display the destination of movement that is predictable from the initial movement. In the prescribed spot jump display of the mouse cursor C, the mouse cursor C entering a prescribed area is subjected to jump-display in another prescribed area. In the incorporated movement of the mouse cursor C, once the data is dragged to a work area associated with a prescribed process, the processing of the dragged data with respect to the preliminarily instructed work incorporation destination is incorporated. As an associated process, for example, setting up a hyperlink is cited.

Figure 3:
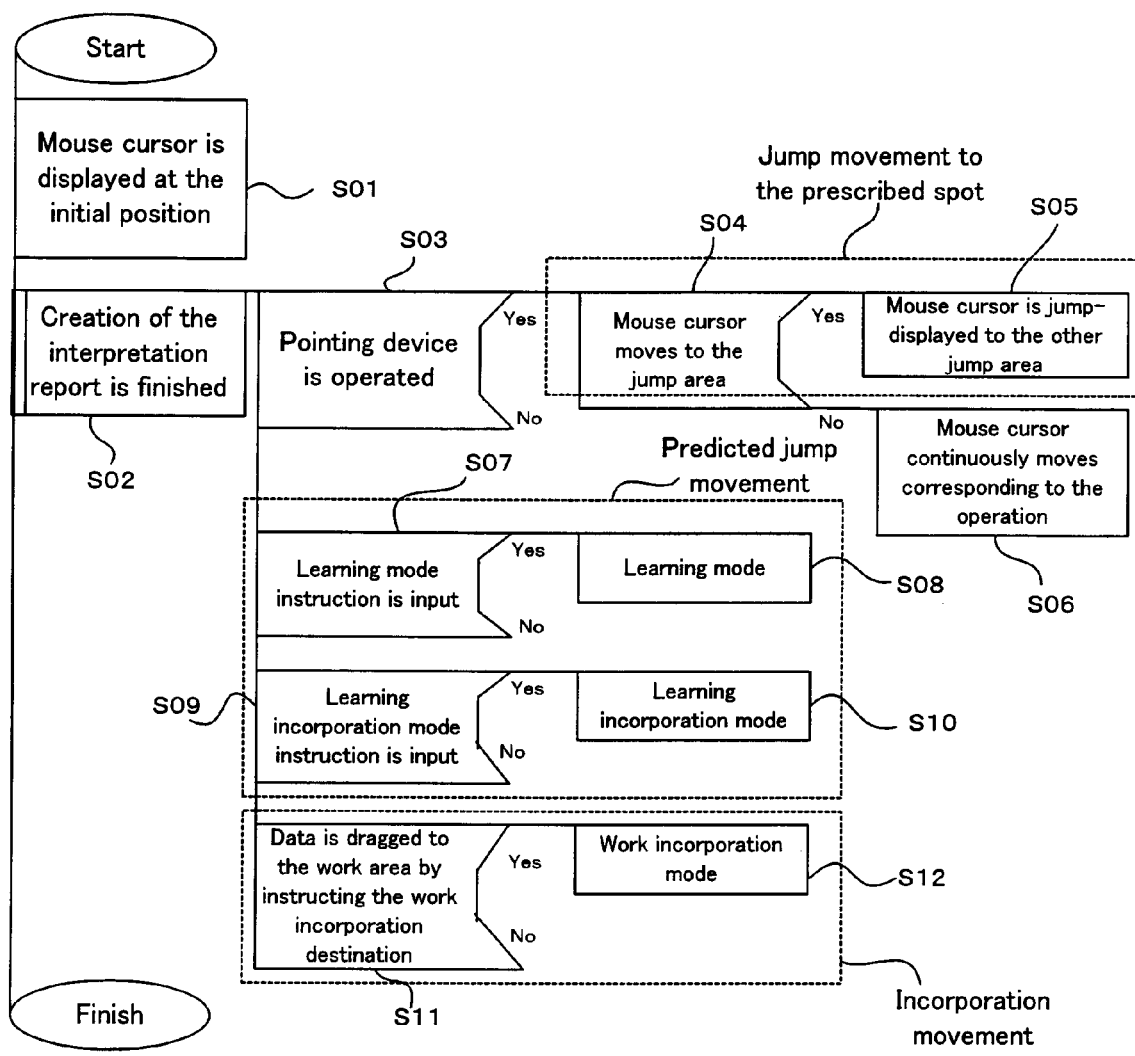
FIG. 3 shows various movement processes of a cursor.

FIG. 3 is a PAD chart showing various movement processes of the mouse cursor C. First, when the medical image interpreting apparatus 1 is started by the operator, the mouse cursor C is displayed at the initial position (S01). The initial position corresponds to the coordinates' position data that has been preliminarily set.

Once the medical image interpreting apparatus 1 is started, an instructing operation to obtain a medical image P is performed using the pointing device 6 or the keyboard 7. In accordance with the operation, from the image server through the communication controller 8 and the network N, the medical image P is obtained and temporarily stored in the main storage part 3. The medical image P that has been stored temporarily in the main storage part 3 is displayed on the monitor 5 after having been converted to a display signal. The operator creates the interpretation report R by interpreting the medical image P while enlarging/reducing the size, or changing its image quality.

Until the creation of the interpretation report R is complete (S02), the arithmetic control part 2 generates interruption processing to move the mouse cursor C in accordance with the signal output from the pointing device 6 or from the keyboard 7 (S03-S12). Furthermore, the arithmetic control part 2 receives the signal output from the pointing device 6 or the keyboard 7 through an input/output controller, while the signal is received in the form of a code generated by the input/output controller.

By operating the pointing device 6 (S03, Yes), once the mouse cursor C is moved to a jump area that is to be set on a display screen of the monitor 5 (S04, Yes), the arithmetic control part 2 performs jump movement control so that the mouse cursor C is subjected to jump-display in the other jump area (S05).

On the other hand, in the case where the destination of movement of the mouse cursor C is not in a jump area (S04, No), the arithmetic control part 2 performs normal jump control to continuously move the mouse cursor C corresponding to the operation of the pointing device 6 (S06).

In the normal movement control, the arithmetic control part 2 receives the coordinates' position data output from the pointing device 6 and allows the mouse cursor C to be displayed at the coordinates' position indicated in the coordinates' position data. The coordinates' position data is continuously output following the operation of the pointing device 6. Then, the arithmetic control part 2 outputs a signal to the monitor 5 to display the mouse cursor C at the coordinates' position indicated in the coordinates' position data.

In addition, for example, if a specific operation for a learning mode instruction such as pressing the F1 key is detected (S07, Yes), the arithmetic control part 2 rolls out a learning mode program stored in the external storage part 4 into the main storage part 3 for interpretation and execution. The medical image interpreting apparatus 1 then enters the learning mode for the predicted jump movement control (S08).

In the learning mode, prediction information for predicting the destination of movement from the initial movement of the mouse cursor C is accumulated.

Furthermore, as an example, if a specific operation for a learning incorporation mode instruction such as pressing the F2 key is detected (S09, Yes), the arithmetic control part 2 rolls out a program of the learning incorporation mode stored in the external storage part 4 to the main storage part 3 for interpretation and execution. The medical image interpreting apparatus 1 enters the leaning incorporation mode in which the mouse cursor C is subjected to jump-display in the predicted destination of movement (S10).

In the learning incorporation mode, the destination of movement is retrieved from the prediction information accumulated in the learning mode based on the initial movement of the mouse cursor C so that the mouse cursor C is subjected to jump-display in the retrieved destination of movement.

Moreover, by using the pointing device 6 or the keyboard 7, when a work incorporation destination such as a character string in an interpretation report is instructed and data such as a medical image is dragged to the work area that is being displayed on the monitor 5 (S11, Yes), the arithmetic control part 2 rolls out a program of learning incorporation mode stored in the external storage part 4 to the main storage part 3 for interpretation and execution. The medical image interpreting apparatus 1 enters the learning incorporation mode in which the process associated with the work area is incorporated into the work incorporation destination (S12).

Until the creation of the interpretation report is complete (S02), if the mouse cursor C is moved, or a specific operation via the keyboard 7 or the pointing device 6 is performed, the arithmetic control part 2 executes a program corresponding to the movement or the specific operation so that the mouse cursor C is subjected to normal movement control, jump movement control, predicted jump movement control, or incorporated movement control (S03-S12).

Figure 4:
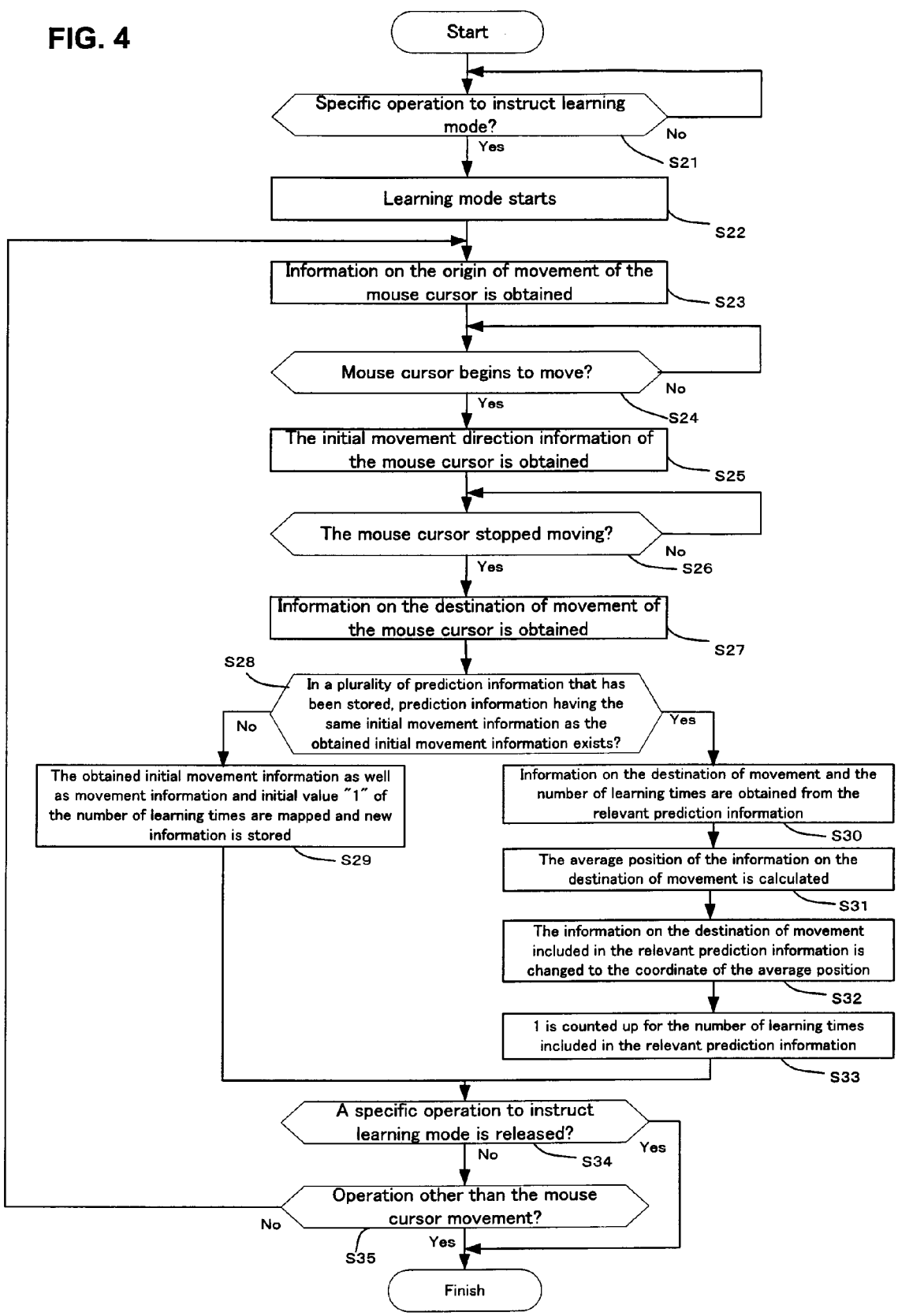
FIG. 4 shows the process of a learning mode in a predicted jump movement.

In such a medical image interpreting apparatus 1, the predicted jump movement is further described in detail. First, the learning mode of the predicted jump movement is described. FIG. 4 is a flow chart showing the process of the learning mode of a predicted jump movement.

First, if a specific operation to instruct the learning mode such as, for example, pressing the F1 key is performed (S21, Yes), the learning mode starts (S22). The arithmetic control part 2 reads out a program of the learning mode from the external storage part 4 and rolls it out to the main storage part 3 for interpretation and execution. The learning mode continues, while the specific operation is being detected from the pointing device 6 or from the keyboard 7.

Once the learning mode starts, the arithmetic control part 2 obtains the information on the origin of movement of the mouse cursor C (S23).

The information on the origin of movement is specified according to the region to which the origin of movement of the mouse cursor C belongs. The coordinate plane of the monitor 5 is preliminarily divided into a plurality of regions. In the external storage part 4, the coordinates' range of each region and the region information, which is an ID of the region, are paired and stored.

Figure 5:
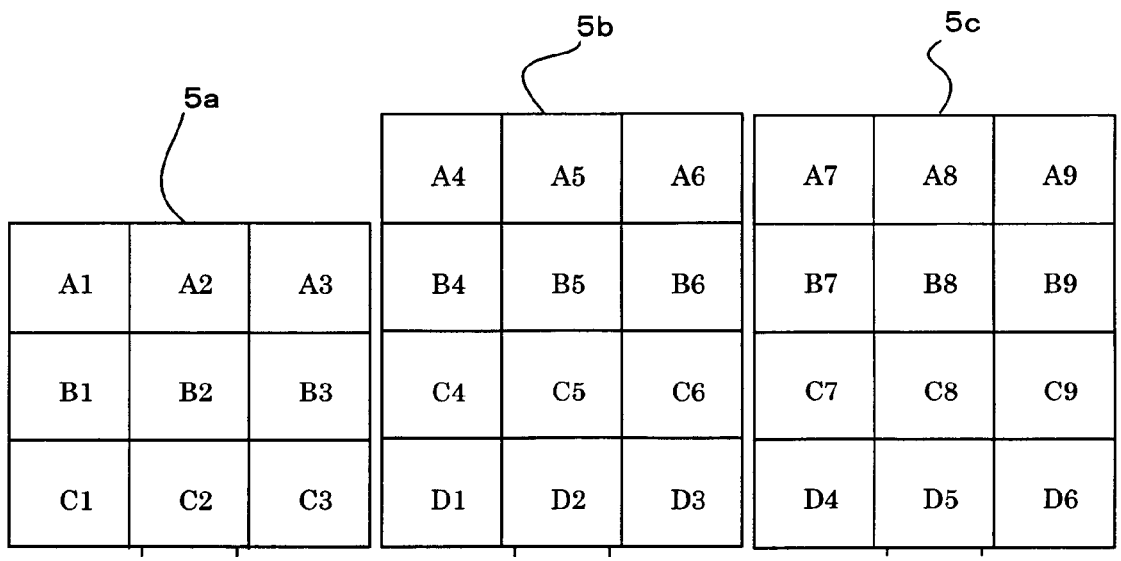
FIG. 5 shows the display screen of a monitor divided into a plurality of regions according to regional information.

FIG. 5 shows schematically a display screen of the monitor 5 that has been divided into a plurality of regions according to region information. The coordinates' plane of the monitor 5 is divided into a plurality of regions described in the region information according to the coordinates' range of each region stored in the external storage part 4. For example, the monitor 5a is divided into region information A1 through C3, the monitor 5b is divided into region information A4 through C6 and D1 through D3, and the monitor 5c is divided into region information A7 through C9 and D4 through D6.

The arithmetic control part 2 compares the coordinates indicated in the coordinates' position data at the time of initial movement that has been stored in the main storage part 3 and the coordinates' range of each region to determine whether the range is beyond or within the region. The region information on the region that is determined as within the range is stored in the main storage part 3 as information on the origin of movement of the mouse cursor C.

Prompted by the operation of the pointing device 6, when the mouse cursor C begins to move (S24, Yes), the arithmetic control part 2 obtains initial movement direction information on the mouse cursor C (S25).

The initial movement direction information shows the direction in which the mouse cursor C has initially moved. The movement direction is specified by any one of the directions derived by plurally dividing omniazimuth directions. In the external storage part 4, a directional vector of each direction and the direction information which is the ID of the direction are paired and stored.

Figure 6:
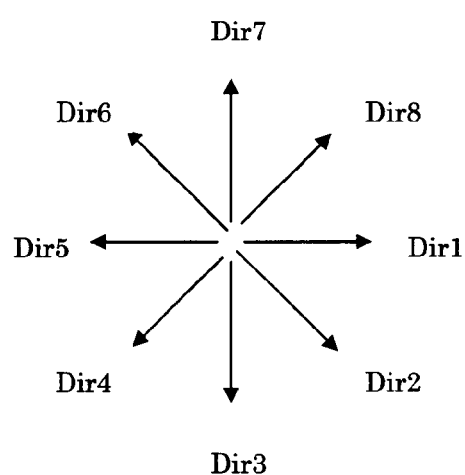
FIG. 6 shows a plurality of directions divided according to directional information.

FIG. 6 shows directions derived by a plurality of divisions made in accordance with the direction information. For example, by the direction information Dir 1 through 8 for dividing the omniazimuth directions into eight directions, the movement direction is specified by any one of Dir 1 through 8 with the closest directional vector.

The arithmetic control part 2 calculates the movement direction at the time of the initial movement from the coordinates' position data before and after the initial movement. The calculated movement direction and each directional vector are compared, and the direction information paired with the closest directional vector is stored in the main storage part 3 as the initial movement direction information.

The information on the origin of movement and the initial movement direction information are paired and stored as initial movement information. FIG. 7 is an example showing the initial movement information stored in the main storage part 3 accompanied by the initial movement of the mouse cursor C. For example, in the main storage part 3, accompanied by the initial movement of the mouse cursor C, the information on the origin of movement C8 and the initial movement direction information Dir 8 are paired and stored.

Once the initial movement information is obtained, the arithmetic control part 2 monitors the stop movement of the mouse cursor C. Once the mouse cursor C stops moving (S26, Yes), the arithmetic control part 2 obtains the information on the destination of movement (S27).

The arithmetic control part 2 samples the coordinates' position data to be stored in the main storage part 3, and when the values show no difference, then it is determined that the movement of the mouse cursor C has stopped. The information on the destination of movement is the coordinate when the mouse cursor C has stopped moving. When it is determined to have stopped, the arithmetic control part 2 obtains the coordinates' position data at the time of stopping from the main storage part 3, to be stored in the main storage part 3 as information on the destination of movement.

FIG. 8 is an example showing the information on the destination of movement stored in the main storage part 3 accompanied by the stop movement of the mouse cursor C. For example, in the main storage part 3, (3089, 502) is stored as the information on the destination of movement (X1, Y1).

Once the initial movement information and the information on the destination of movement are obtained, the arithmetic control part 2 creates prediction information to be stored in the external storage part 4 (S28 through S33). The prediction information is information showing the destination movement with respect to the initial movement of the mouse cursor C. The prediction information allows the initial movement information, information on the destination of movement, and the number of learning times to link together.

FIG. 9 is a figure showing prediction information stored in the external storage part 4. For example, the prediction information allows the information on the destination of movement C8, the initial movement direction information Dir 8, (3100, 500) as the information on the destination of movement (X2, Y2), and the number of learning times 8 to link together.

The arithmetic control part 2 retrieves the existence of prediction information having the same initial movement information from a plurality of prediction information stored in the external storage part 4 (S28). If relevant prediction information does not exist (S28, No), the initial movement information and the movement information that have been obtained and the initial value "1" of the number of learning times are linked to store the new prediction information in the external storage part 4 (S29).

If the prediction information having the same initial movement information exists (S28, Yes), the information on the destination of movement (X2, Y2) and the number of learning times are obtained from the relevant prediction information (S30), to which newly obtained information on the destination of movement (X1, Y1) in the learning mode is added to calculate the average position (X3, Y3) (S31).

The average position (X3, Y3) is a coordinate of the average position of the destination of movement in each initial movement of the mouse cursor C that appears in the same initial movement information. To be concrete, the calculation of the average position (X3, Y3) is obtained by calculating the following Formula 1. Herein, the average position to be obtained is (X3, Y3), the information on the destination of movement obtained in the learning mode presently is (X1, Y2), the information on the destination of movement included in the prediction information that has been already stored is (X2, Y2), and the number of learning times is N.

$$(X3, Y3) = \{(X1, X2) + (X2, Y2) \times N\}/(N+1) \quad \text{Formula 1:}$$

When the average position (X3, Y3) is calculated, the arithmetic control part 2 changes the information on the destination of movement (X2, Y2) included in the prediction information that is relevant in the retrieval of S28 to the coordinate of the average position (X3, Y3) (S32), and "1" is counted for the number of learning times (S33).

FIG. 10 shows prediction information into which the movement of the mouse cursor C of the current time has been incorporated.

Accompanied by the movement of the mouse cursor C of the current time, it is presumed that as initial movement information, the information on the origin of movement C8 and the initial movement direction information Dir 8 have been stored and the information on the destination of movement (X1=3089, Y1=502) has been obtained. Also, prediction information including the information on the destination of movement C8 and the initial movement direction information Dir 8, the information on the destination of movement (X2=3100, Y2=500), and the number of learning times 8 is presumed to have been stored in the external storage part 4.

The initial movement information included in the prediction information and the initial movement information obtained accompanying the movement of the mouse cursor C of the current time are the same, and thus, the prediction information is found relevant by the retrieval.

As shown in FIG. 10, from the information on the destination of movement and the number of learning times that make up the prediction information, and from the information on the destination of movement obtained from the movement of the mouse cursor C of the current time, the average position (3098, 500) is calculated, and the information on the destination of movement included in the prediction information is updated to the calculated average position (3098, 500). Furthermore, "1" is counted for the number of learning times, and updated to the number of learning times 9.

While a specific operation to instruct the learning mode is not released (S34, No), and while an operation other than the movement of the mouse cursor C such as, for example, pressing or releasing the button provided with the pointing device 6 (S35, No) is not performed, every time when the mouse cursor C starts/stops moving, S23 through S33 are repeated. When the specific operation instructing the learning mode is released (S34, Yes) or when operations other than the movement of the mouse cursor C are performed (S35, Yes), the learning mode ends.

Figure 11:
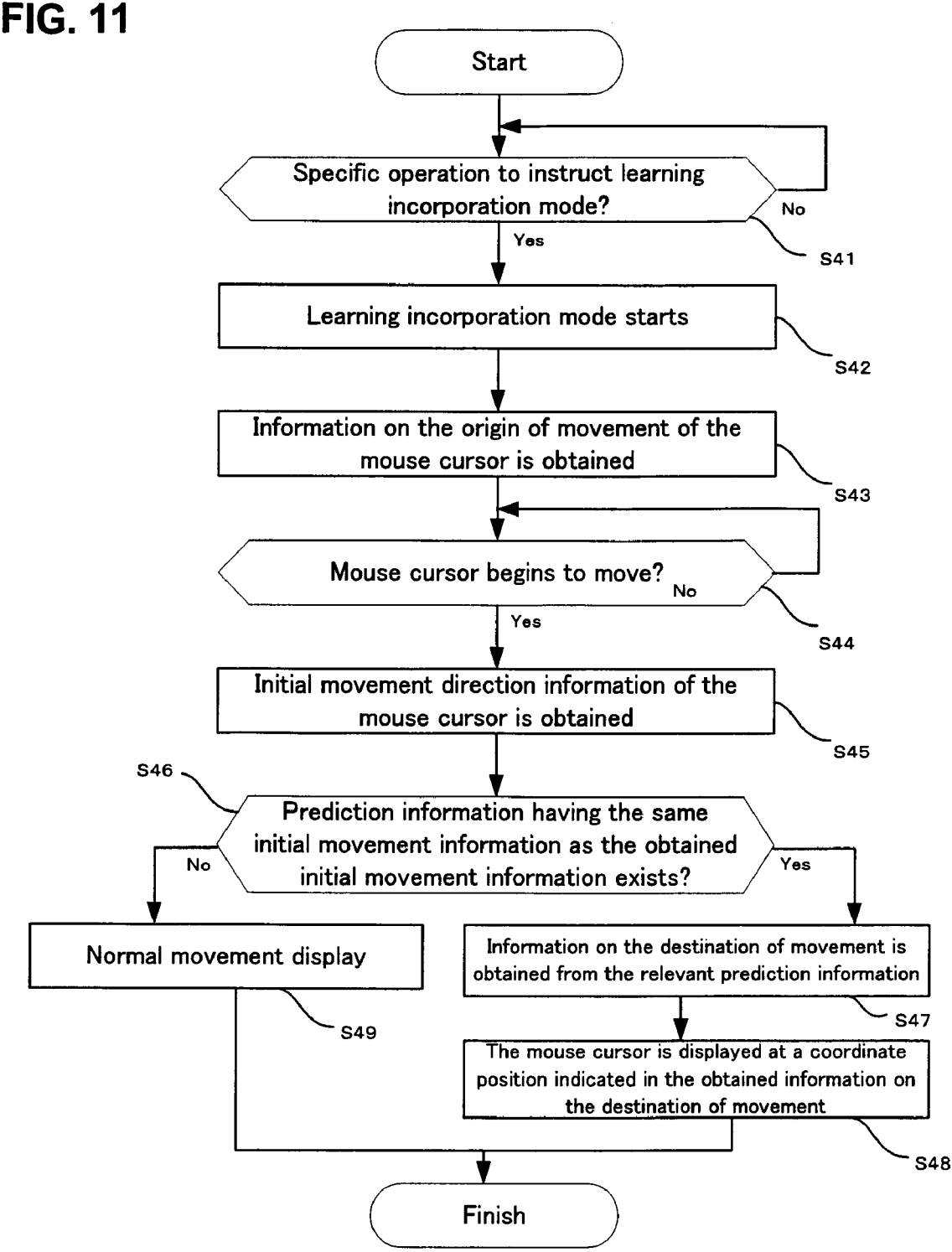
FIG. 11 shows an incorporation process of a predicted jump movement in the learning mode.

The learning incorporation mode of predicted jump movement is described. FIG. 11 is a flow chart showing a learning incorporation mode process of a predicted jump movement.

First, once a specific operation to instruct the learning incorporation mode such as, for example, pressing the F2 key (S41, Yes) is performed, the learning incorporation mode starts (S42). The arithmetic control part 2 reads out a learning incorporation mode program from the external storage part 4 and rolls it out to the main storage part 3 for interpretation and execution. While the specific operation is being detected from the pointing device 6 or from the keyboard 7, the learning incorporation mode continues.

When the learning incorporation mode starts, the arithmetic control part 2 obtains the information on the origin of movement of the mouse cursor C (S43).

Furthermore, in the learning incorporation mode, the information on the origin of movement is specified by the divided region according to the region information. The arithmetic control part 2 compares the coordinate indicated in the coordinates' position data at the time of the initial movement that has been stored in the main storage part 3 and the coordinates' range of each region to determine whether the range is beyond or within the region. The region information on the region that is determined as within the range is stored in the main storage part 3 as information on the origin of movement of the mouse cursor C.

Prompted by the operation of the pointing device 6, when the mouse cursor C begins to move (S44, Yes), the arithmetic control part 2 obtains the initial movement direction information on the mouse cursor C (S45).

Even in the learning incorporation mode, the initial movement direction information is specified by any one of the directions divided according to the direction information. The arithmetic control part 2 calculates the movement direction of the initial movement from the coordinates' position data before and after the initial movement. The calculated movement direction and the directional vector are compared, and the direction information paired with the closest directional vector is stored in the main storage part 3 as initial movement direction information.

In the main storage part 3, accompanied by the initial movement of the mouse cursor C, the information on the origin of movement and the initial movement direction information are paired and stored. That is, the information on the origin of movement and the initial movement direction information related to the initial movement of the mouse cursor C are obtained as initial movement information.

Once the initial movement information is obtained, the arithmetic control part 2 retrieves prediction information from the prediction information stored in the external storage part 4, having the same initial movement information as the initial movement information stored in the main storage part 3 (S46). If the prediction information having the same initial movement information exists (S46, Yes), the information on the destination of movement is obtained from the relevant prediction information (S47).

Once the information on the destination of movement is obtained, while regarding the obtained information on the destination of movement as a coordinates' position data, the arithmetic control part 2 displays the mouse cursor C at the coordinates' position indicated in the information on the destination of movement as a coordinates' position data (S48). Furthermore, in the case of non-existence (S46, No), the mouse cursor C is subjected to a normal movement (S49).

Figure 12A:
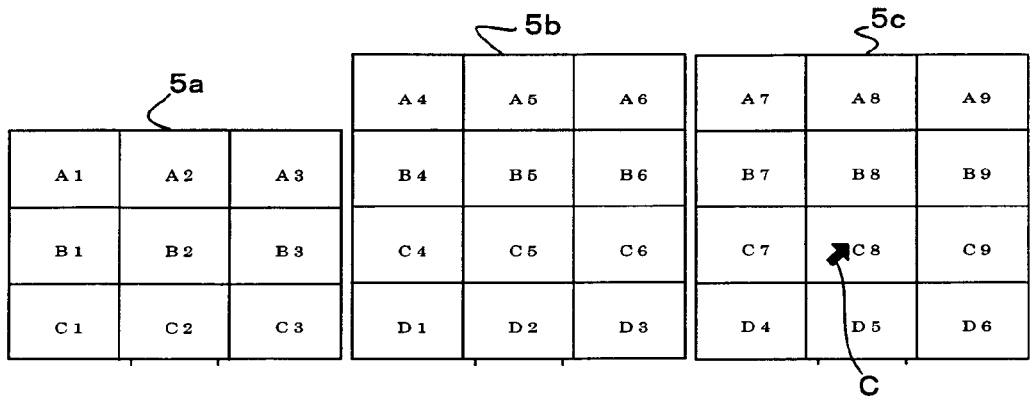
FIG. 12A shows the start of the learning incorporation mode.
Figure 12B:
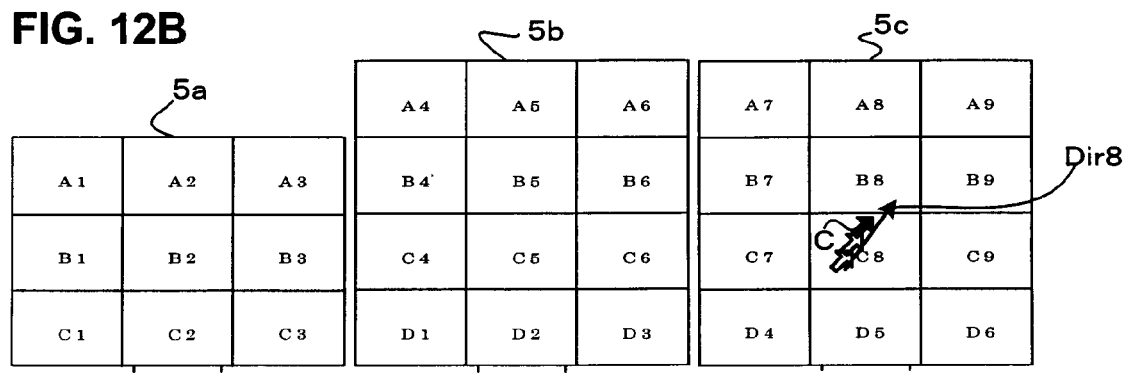
FIG. 12B shows the mode at the time of initial movement of the cursor C.
Figure 12C:
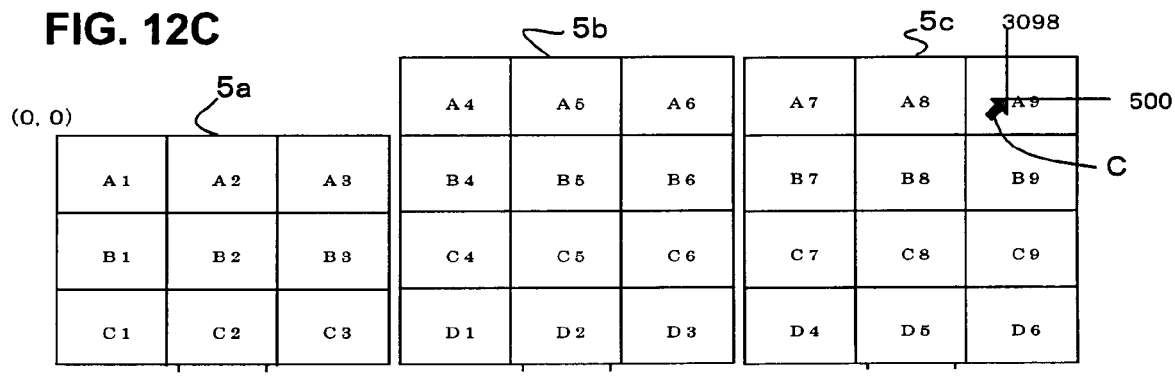
FIG. 12C shows the mode at the time of jump-display of the cursor C.

FIG. 12 shows contents displayed by the monitor 5 in the learning incorporation mode: FIG. 12A shows the state at the start of the learning incorporation mode, FIG. 12B shows the state at the time of the initial movement of the mouse cursor C, and FIG. 12C shows the state at the time of jump-display of the mouse cursor C.

As shown in FIG. 12A, at the start of the learning incorporation mode, the mouse cursor C is being displayed in a region specified by the region information C8. When the pointing device 6 is operated, as shown in FIG. 12B, the mouse cursor C begins to move corresponding to the operation of the pointing device 6. For example, the mouse cursor C begins to move in the direction of the direction information Dir 8 at the time of the initial movement.

FIG. 13 is an example showing the initial movement information stored in the main storage part 3 accompanied by the initial movement of the mouse cursor C. The mouse cursor C enters the learning mode in a state of being displayed in a region specified by the region information C8, and in the initial movement the mouse cursor C begins to move in the direction of the direction information Dir 8. Due to this, the information on the origin of movement C8 and the initial movement direction information Dir 8 are stored as a pair in the main storage part 3.

FIG. 14 is an example showing prediction information stored in the external storage part 4. For example, in the external storage part 4, the information on the destination of movement C8, the initial movement direction information Dir 8, (3098, 500) as information on the destination of movement (X2, Y2), and the number of leaning times 9 are linked and stored as prediction information. The initial movement information stored in the main storage part 3 and the initial movement information that the information on the destination of movement are the same, hence, retrieved by the arithmetic control part 2, (3098, 500) is obtained as information on the destination of movement.

When the information on the destination of movement (3098, 500) is obtained, as shown in FIG. 12C, the mouse cursor C is jump-displayed to the position corresponding to the coordinate (3098, 500) after the initial movement.

As described, according to the predicted jump-movement display of the mouse cursor C of the medical image interpreting apparatus 1 related to the present embodiment, the information on the destination of movement in which the initial movement information that has been preliminarily stored and the information in the subject are linked, prompts the jump-display to the destination movement, in the case of the presence of the initial movement of the mouse cursor C matched with the initial movement information, regarding that a movement to the destination movement indicated in the information on the destination of movement is about to take place.

Therefore, just by slightly moving the mouse cursor C, the mouse cursor C jumps to the desired destination movement, thus, it becomes possible to omit an operation of the pointing device 6 in between. Due to this, the operation load of the pointing device 6 is reduced, preventing an operator's thought from being disrupted in creating an interpretation report, thus, enhancing interpretation efficiency and reducing interpretation mistakes.

Furthermore, since the initial movement and the destination movement of the mouse cursor C may be learned in the learning mode, it becomes possible to increase the degree of certainty of a predictable movement direction.

Furthermore, the origin of movement is to be determined by the region and the initial movement direction is to be determined by the direction of fixed sections that have been divided, therefore, even if the origin of movement and the initial movement direction do not completely match by the unit of coordinate, the destination of movement becomes predictable. Since high resolution is required for a medical image display, in the case of perfect match by the unit of coordinate, the volume of prediction information becomes significantly large, and there is a concern that the prediction may not be able to catch up with the movement of the mouse cursor C, depending on the search load of the prediction information; however, according to the present embodiment, the mouse cursor C may be swiftly jump-displayed.

Figure 15:
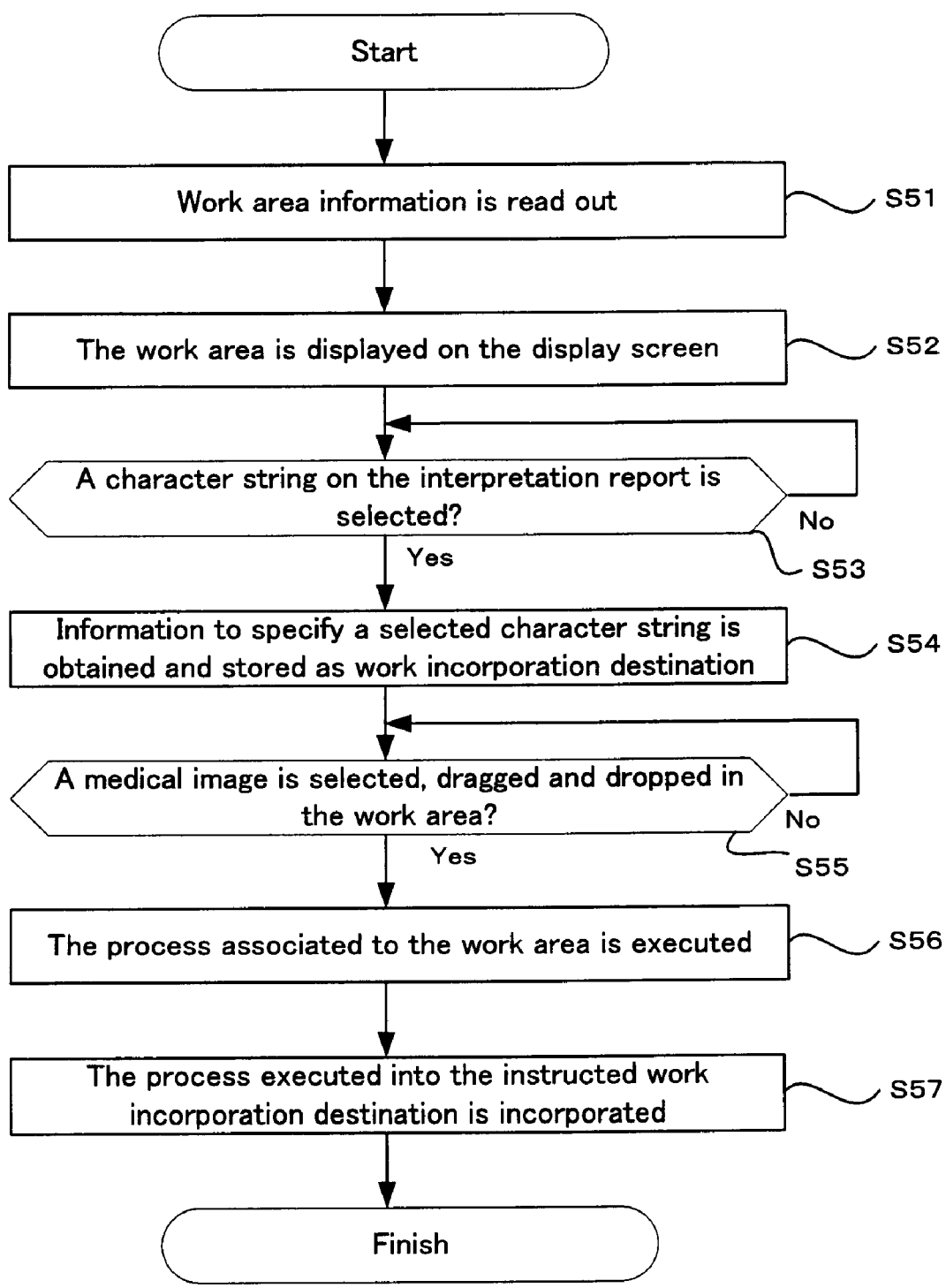
FIG. 15 shows an incorporated movement process.

Next, the incorporated movement mode is described in detail. FIG. 15 is a flow chart showing an incorporated movement process.

First, the arithmetic control part 2 reads out work area information stored in the external storage part 4 (S51) and displays the work area on a display screen of the monitor 5 (S52).

Figure 16:
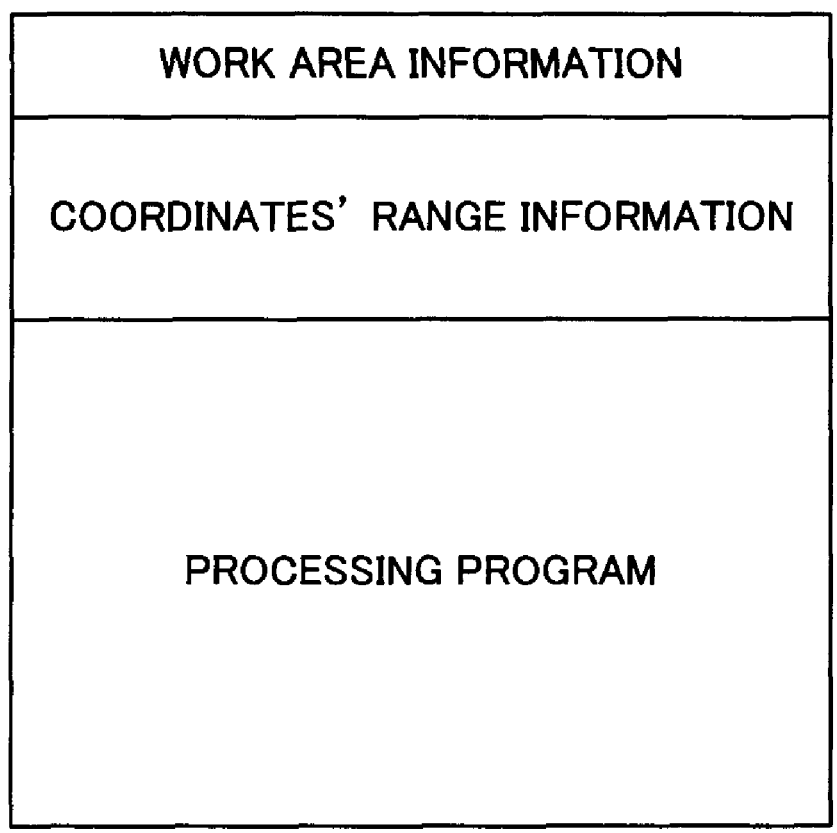
FIG. 16 shows work area information.

In the external storage part 4, work area information is preliminarily stored. FIG. 16 shows work area information. As shown in FIG. 16, the work area information is the coordinates' range information on a spot where the work area is to be displayed and a processing program associated with the coordinates' range information. The processing program writes the process of data that has been dragged into the work area.

The arithmetic control part 2 obtains the work area information from the external storage part 4 and holds a storage region of the work area information in the main storage part 3 for rolling out to the region. The coordinates' range information is read out from the work area information and the work area is displayed in the coordinates' range indicated in the coordinates' range information. The coordinate range's information is set in the proximity of the region where a medical image P is to be displayed.

Figure 17A:
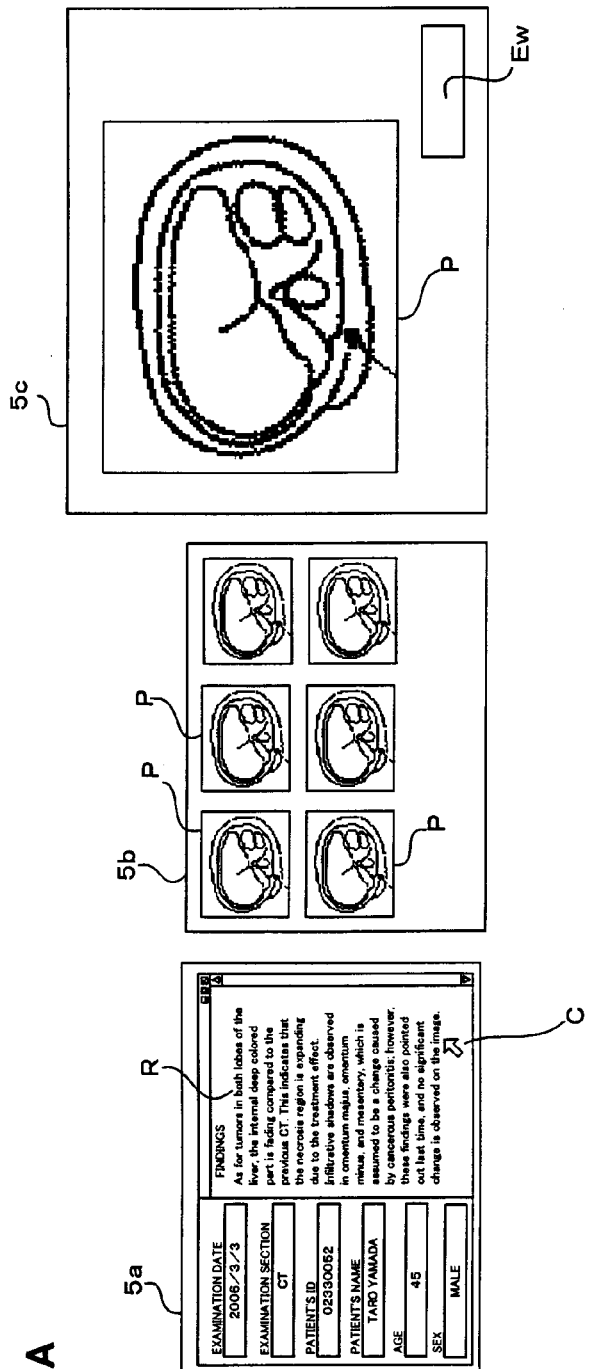
FIG. 17A shows a state in which a work area is being displayed.

FIG. 17A shows a state in which a work area is being displayed. As shown in FIG. 17A, the work area Ew is displayed in a spot indicated on the display screen. For example, as described later, in the case of having a hyperlink process associated with the work area Ew, it is suitable to display the work area Ew in the proximity of the medical image P that is being displayed.

By operating the pointing device 6, when a character string on an interpretation report is selected (S53, Yes), the arithmetic control part 2 obtains information indicating the position, range, and so forth specifying the selected character string, which is to be stored in the main storage part 3 as a work incorporation destination (s54).

In instructing the work incorporation destination, by operating the pointing device 6, when a medical image is selected, dragged and dropped into a work area (S55, Yes), the arithmetic control part 2 executes a process associated with the work area (S56), and incorporates the executed process to the instructed work incorporation destination (S57).

Once the medical image is dragged into the work area, the arithmetic control part 2 reads out a processing program from the work area information on the work area for interpretation and execution. If the processing program is, for example, a hyperlink process, the hyperlink of the medical image is set with respect to the selected character string.

Figure 17B:
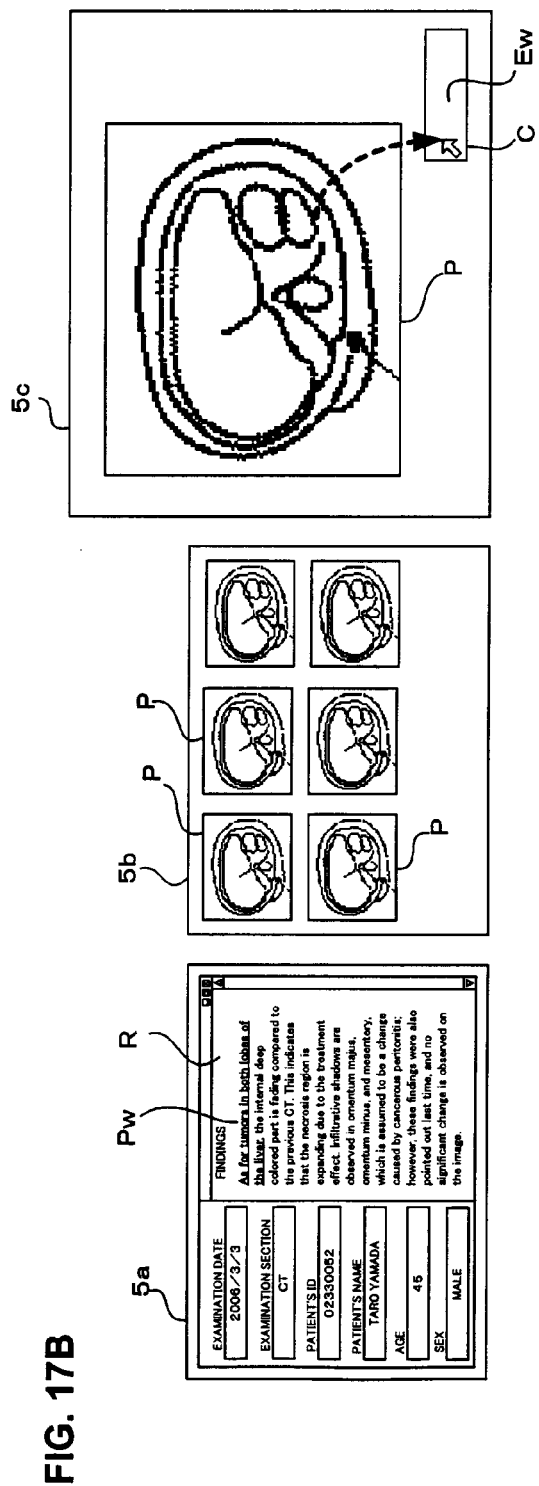
FIG. 17B shows dragging of a medical image to a work area and setting of a hyperlink.

FIG. 17B shows dragging of a medical image into a work area and setting of the hyperlink. As shown in FIG. 17B, when a character string on an interpretation report is selected as a work incorporation destination Pw, the fact that the selection has been made is visually acknowledged by changing the basic color of the character string to gray, for example. When the medical image is dragged and dropped into the work area, the color of the character string of the work incorporation destination Pw changes to, for example, blue, and underlining is drawn to distinctively display that the hyperlink has been set.

FIG. 18 shows a work incorporation destination into which a hyperlink process associated with the work area is incorporated. The arithmetic control part 2 obtains a link destination such as the address information on a medical image so that the link destination of a dragged medical image is carried in the portion of the character string, that is, a work incorporation destination in the data of an interpretation report.

As described, according to the incorporated movement of the mouse cursor C of the medical image interpreting apparatus 1 related to the present embodiment, by associating a prescribed process such as a hyperlink with a work area and by dragging the data into the work area after designating the work incorporation destination, the process associated with the work area is incorporated into the work incorporation destination.

Therefore, since the work incorporation destination and the data to be processed are both selected for the prescribed process, the reciprocating movement of the mouse cursor C between the work incorporation destination and the data is no longer required; accordingly it becomes possible to reduce the operational volume of the pointing device 6. Due to this, the operational load of the pointing device is reduced, achieving enhancement in interpretation efficiency and a reduction of interpretation mistakes without disrupting an operator's thought in creating an interpretation report.

Figure 19:
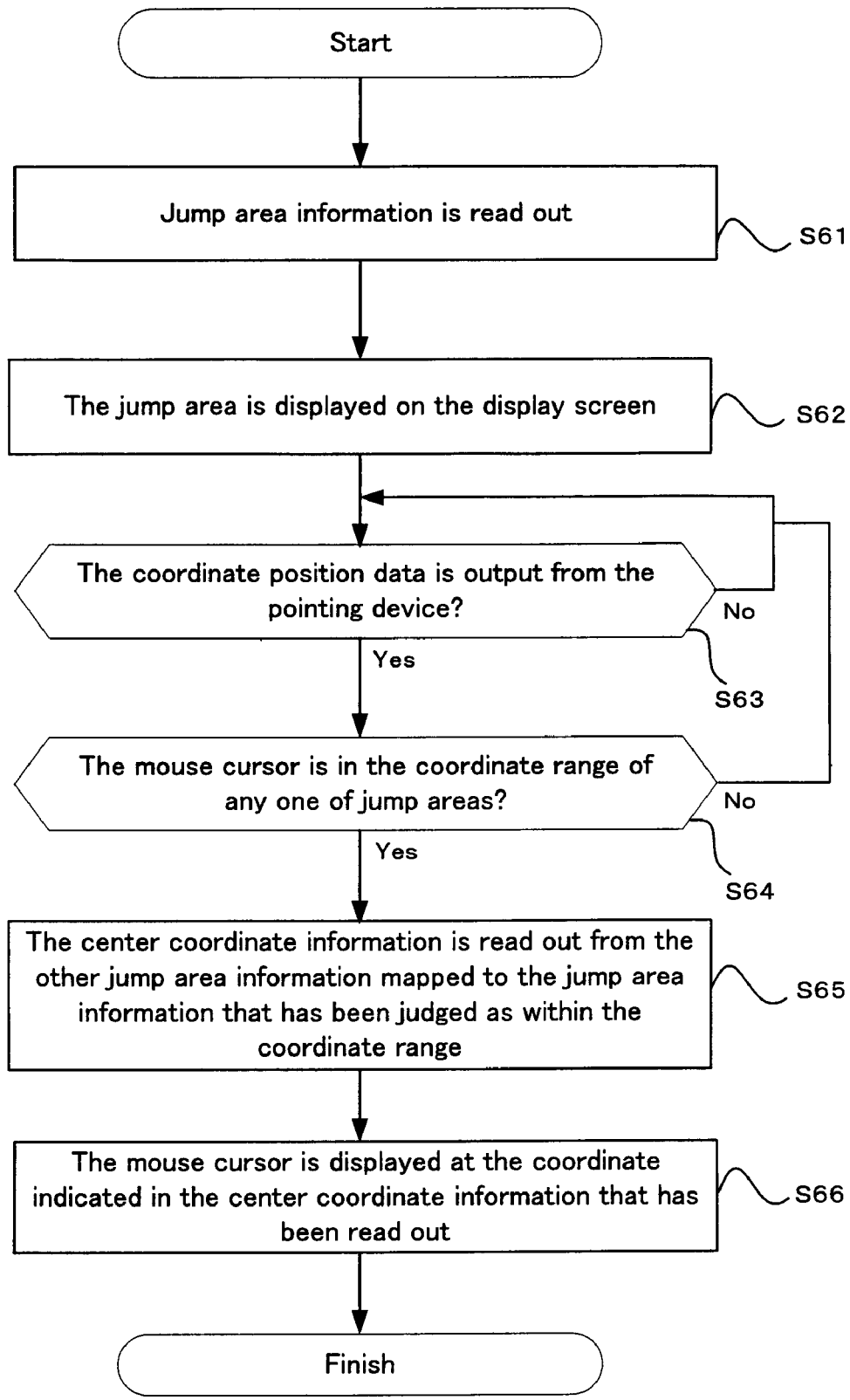
FIG. 19 shows a jump movement process.

Next, a prescribed spot jump movement is described in further detail. FIG. 19 is a flow chart showing a prescribed spot jump movement process.

First, the arithmetic control part 2 reads out jump area information stored in the external storage part 4 (S61), and operates to allow the jump area to be displayed on a display screen of the monitor 5 (S62).

In the external storage part 4, preliminarily jump area information is stored. FIG. 21 is a figure showing jump area information stored in the external storage part 4. As shown in FIG. 21, the jump area information is coordinate range information indicating a spot on a display screen. Furthermore, the coordinate range information carries center coordinate information indicating the center coordinate of the coordinate range. In the external storage part 4, a plurality of jump area information is stored, and one jump area information is linked to the other jump area information, one to one. The set of jump area information mutually provides the exit/entry of the mouse cursor C to each other.

The arithmetic control part 2 obtains both of paired jump information from the external storage part 4 and holds a storage region of the jump area information in the main storage part 3 for rolling out to the region. The coordinate range information is read out from both of jump area information and the jump area is displayed respectively in the coordinate range indicated in the coordinate range information.

Figure 20A:
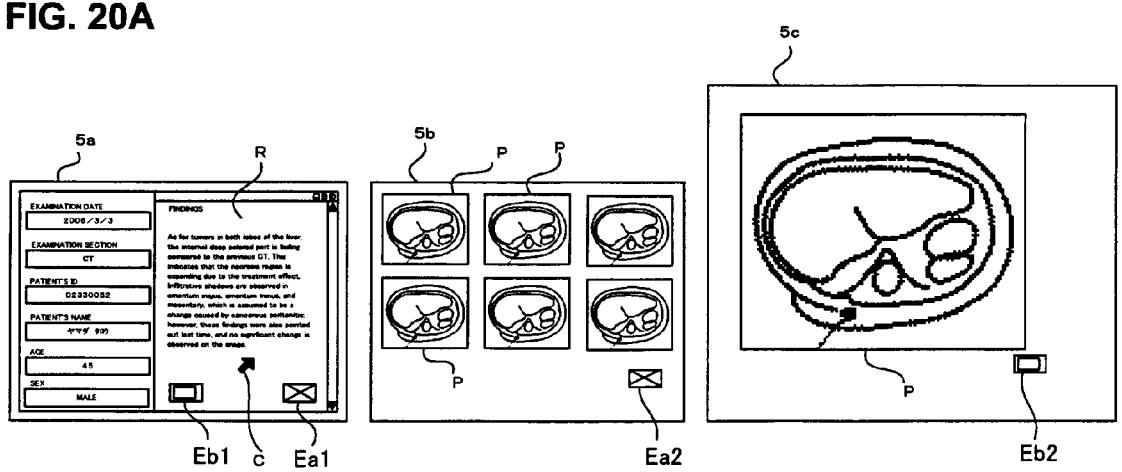
FIG. 20A shows a state in which a jump area is being displayed.

FIG. 20A shows a state in which jump areas are being displayed. As shown in FIG. 20A, in a spot indicated by the jump area information on the display screen, jump areas Ea1, Ea2, Eb1, and Eb2 are displayed. A plurality of groups of jump areas namely Ea and Eb that have been stored in the external storage part 4 are displayed. A set of the jump areas Ea and Eb are designed in the same form and displayed, therefore, the set of jump areas Ea and Eb are visually recognizable.

When coordinate position data is output from the pointing device 6 (S63, Yes), the arithmetic control part 2 compares the coordinate range indicated in each jump area information that has been rolled out in the main storage part 3 and the coordinate indicated in the coordinate position data to determine whether the mouse cursor C is within the coordinate range of any one of jump areas (S64).

Figure 20B:
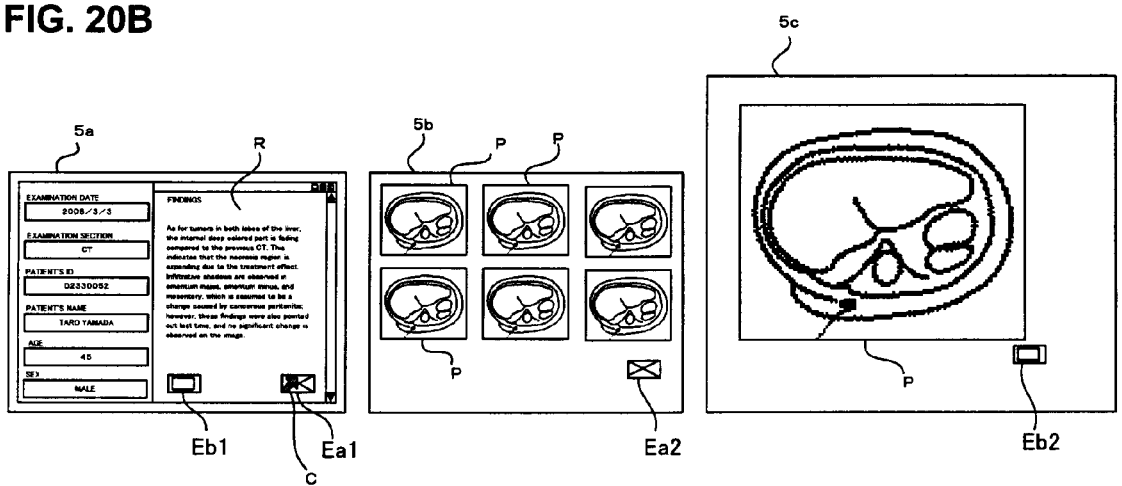
FIG. 20B shows a state in which the cursor has entered a jump area.

FIG. 20B shows a state in which the mouse cursor C has entered into the jump area Ea1. As shown in FIG. 20B, when the mouse cursor C moves and is positioned on the jump area Ea1, it is determined that the mouse cursor C has entered into the jump area Ea1.

When it is determined that the coordinate indicated in the coordinate position data is within the coordinate range indicated in any one of jump area information (S64, Yes), the arithmetic control part 2 reads out center coordinate information from the other jump area information linked to the jump area information that has been determined as within the coordinate range (S65).

The arithmetic control part 2 regards the center coordinate information that has been read out as coordinate position data and displays the mouse cursor C at the coordinate indicated in the coordinate position data (S66).

Figure 20C:
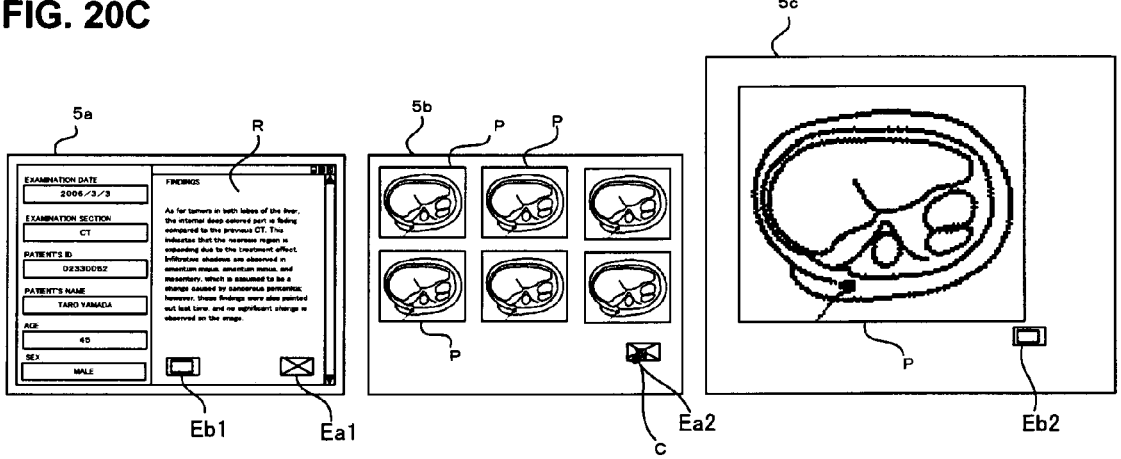
FIG. 20C shows a state in which the cursor has been jump-displayed onto the other jump area.

FIG. 20C shows a state in which the mouse cursor C is jump-displayed in the other jump area. As shown in FIG. 20C, when the mouse cursor C enters into one jump area Ea1, the mouse cursor C is subjected to jump-display onto the other jump area Ea2 of the same state that has been related to the jump area Ea1.

As described, according to the jump movement display of the mouse cursor C of the medical image interpreting apparatus 1 related to the present embodiment, when the mouse cursor C enters into any one of the set of jump areas, the mouse cursor C is jump-displayed in the other jump area.

Therefore, just by moving the mouse cursor C onto one jump area, the mouse cursor C appears on the other distant jump area. The operation of the pointing device 6 in between may be omitted. Due to this, the operation load of the pointing device 6 is reduced, thus preventing an operator's thought in creating an interpretation report from being destructed, and the enhancement in interpreting efficiency and the reduction of interpretation mistakes are achieved.

Figure 22:
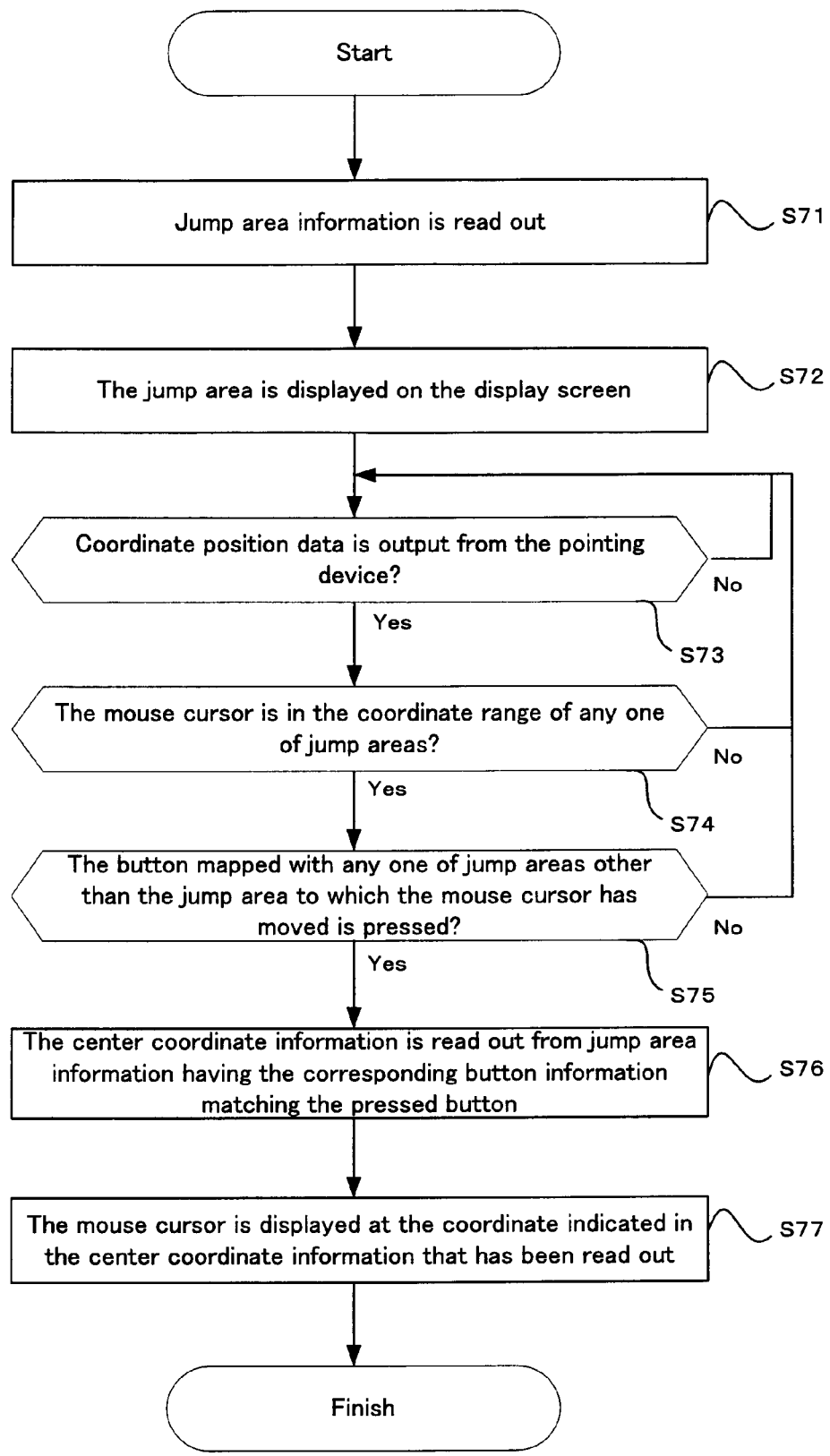
FIG. 22 shows a first modification example of a jump movement process.

Next, a modification example of the prescribed spot jump movement is further described into the details. FIG. 22 is a flow chart showing the prescribed spot jump movement process related to the present modification example.

First, the arithmetic control part 2 reads out jump area information stored in the external storage part 4 (S71), and displays the jump area on a display screen of the monitor 5 (S72).

In the external storage part 4, preliminarily jump area information is stored. FIG. 23 is a figure showing at least a set of jump area information stored in the external storage part 4. In other words, more than two jump area information is stored. As shown in FIG. 23, as for each jump area information, coordinate range information indicating a spot on the display screen and the corresponding button information to distinguish the corresponding button arranged on the keyboard 7 are paired and included. Furthermore, the coordinate range information carries center coordinate information indicating the center coordinate of the coordinate range. In the external storage part 4, a plurality of jump area information is stored and each jump area information has unique corresponding information. That is, a jump area whose display position is provided by the coordinate range information is individually distinguished by the corresponding button information.

The arithmetic control part 2 obtains jump area information from the external storage part 4 and holds a storage region of the jump area information in the main storage part 3 for rolling out to the region. The coordinate range information is read out from both of jump area information and the jump area is displayed respectively in the coordinate range indicated in the coordinate range information.

Figure 24A:
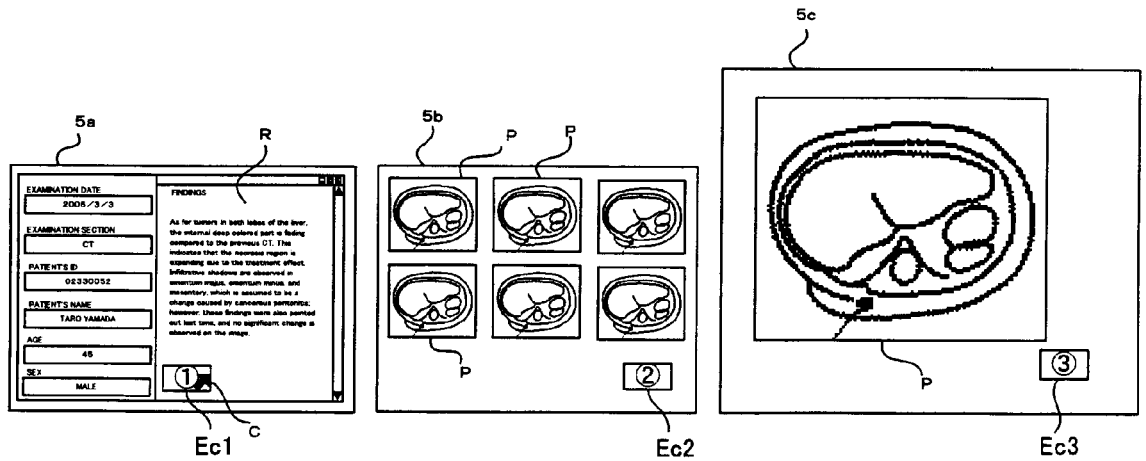
FIG. 24A shows a state in which a jump area is being displayed.

FIG. 24A shows a state in which jump areas are being displayed. As shown in FIG. 24A, in spots indicated in the jump area information on the display screen, jump areas Ec1, Ec2, and Ec3 are displayed. In the jump areas Ec1, Ec2, and Ec3, the name of a button appears in corresponding button information that has been included in the jump area information is being displayed making it possible to visually recognize which button corresponds to which jump area.

When coordinate position data is output from the pointing device 6 (S73, Yes), the arithmetic control part 2 compares the coordinate range indicated in each jump area information that has been rolled out in the main storage part 3 and the coordinate indicated in the coordinate position data to determine whether the mouse cursor C is within the coordinate range of any one of jump areas (S74).

Figure 24B:
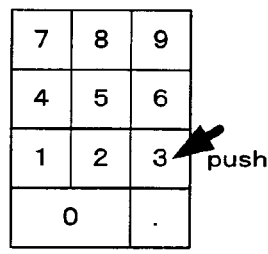
FIG. 24B shows buttons to be arranged on a keyboard.

When it is determined that the coordinate indicated in the coordinate position data is within the coordinate range indicated in any of jump area information (S74, Yes), in a state in which the mouse cursor C has entered into any one of jump areas, as shown in FIG. 24B, if a button that has been linked to any one of jump areas other than the jump area where the mouse cursor C has moved to is pressed (S75, Yes), the arithmetic control part 2 reads out center coordinate information from the jump area information having corresponding button information matched with the pressed button (S76).

The arithmetic control part 2 regards the center coordinate information that has been read out as coordinate position data, and displays the mouse cursor C at the coordinate indicated in the coordinate position data (S77).

Figure 24C:
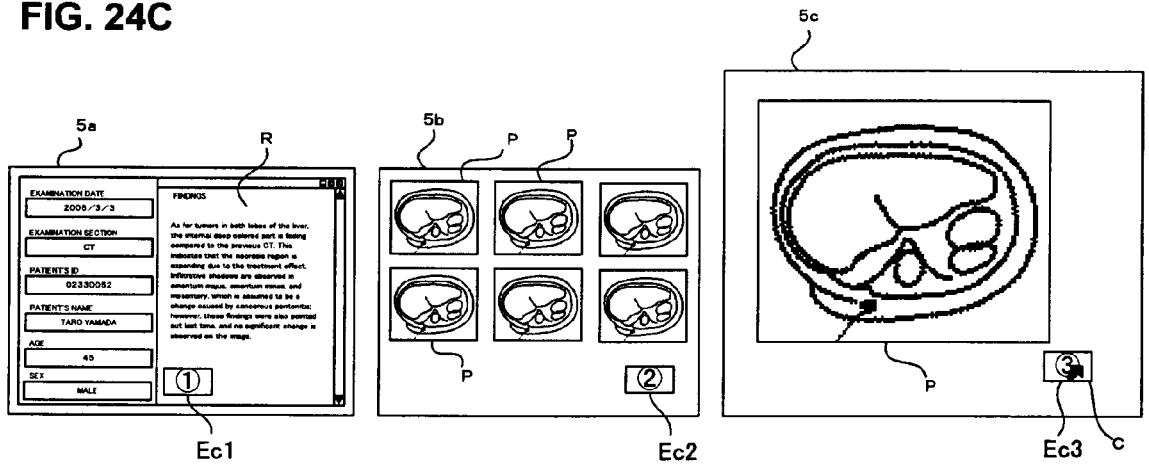
FIG. 24C shows a state in which the cursor has been jump-displayed onto the other jump area.

FIG. 24C shows a state in which the mouse cursor C has been jump-displayed onto the jump area corresponding to the pressed button. As shown in FIG. 24C, when the mouse cursor C moves to the jump area Ec1 and while still in the state if a key "3" that is a button corresponding to the jump area Ec3 is pressed, the mouse cursor C is jump-displayed in the jump area Ec3 that has been linked to "3".

According to the present modification example, just by moving the mouse cursor C onto one jump area and by pressing a button corresponding to the desired jump area to jump to, the mouse cursor C appears onto the desired distant jump area. The operation of the pointing device 6 in between may be omitted. Due to this, the operation load of the pointing device is reduced, thus preventing an operator's thought in creating an interpretation report from being destructed, and the enhancement in interpreting efficiency and the reduction of interpretation mistakes are achieved.

Figure 25:
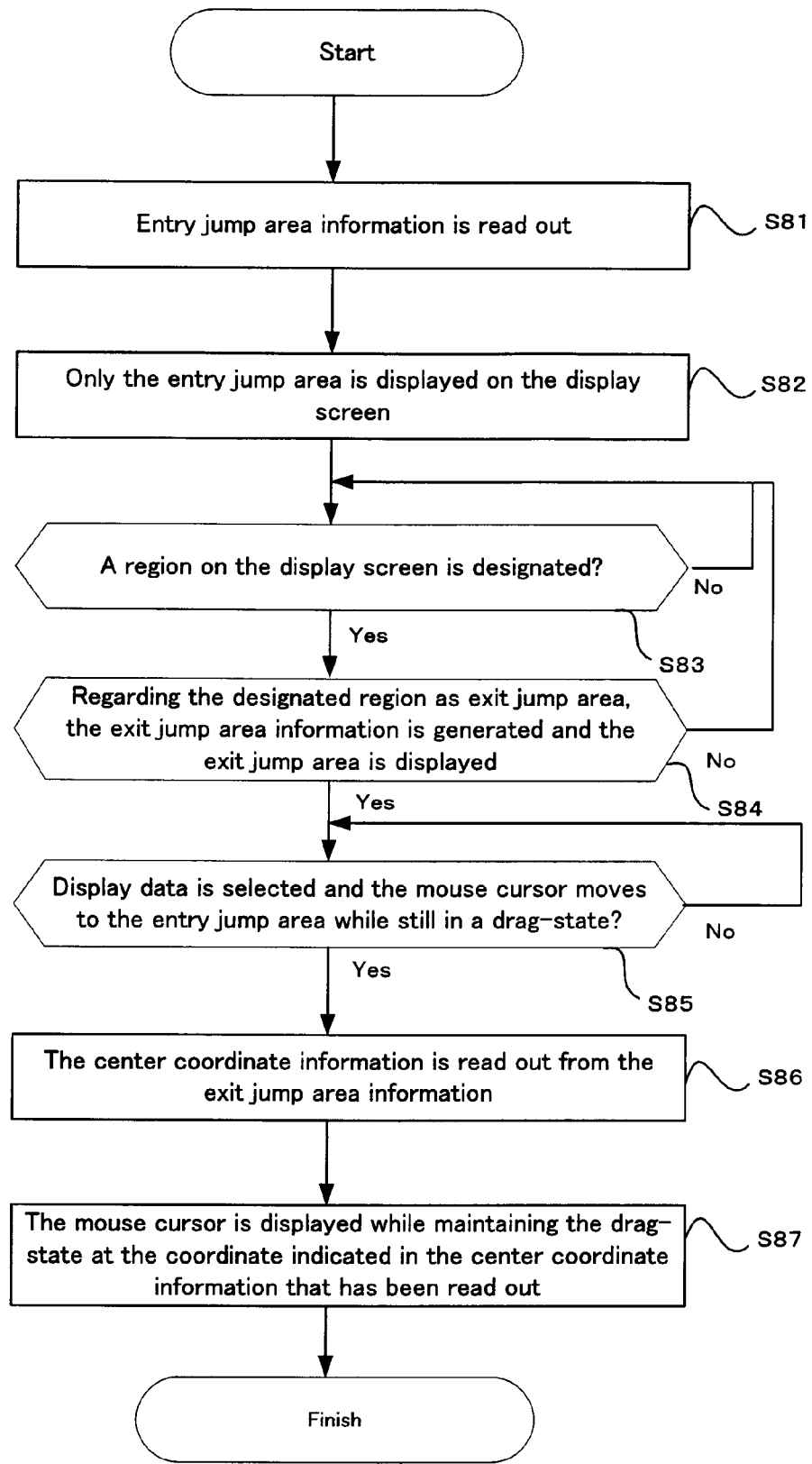
FIG. 25 shows a second modification example of the jump movement process.

Furthermore, other modification example of the prescribed spot jump movement is described into the further details. FIG. 25 is a flow chart showing a prescribed spot jump movement process related to the modification example.

First, the arithmetic control part 2 reads out entry jump area information stored in the external storage part 4 (S81), and displays the entry jump area on a display screen of the monitor 5 (S82).

In the external storage part 4, preliminarily entry jump area information has been stored. FIG. 26A is a figure showing the entry jump area information stored in the external storage part 4. As shown in FIG. 26A, in the modification example, in the region for housing the jump area information, preliminarily only the jump area information on the entry side is stored. In other words, the jump area information on the exit side has not been preliminarily stored, thus not displayed at the beginning.

The arithmetic control part 2 obtains only the entry jump area information from the external storage part 4 and holds a storage region of the entry jump area information in the main storage part 3 for rolling out to the region. The coordinate range information is read out from the entry jump area information and the entry jump area is displayed respectively in the coordinate range indicated in the coordinate range information.

Figure 27A:
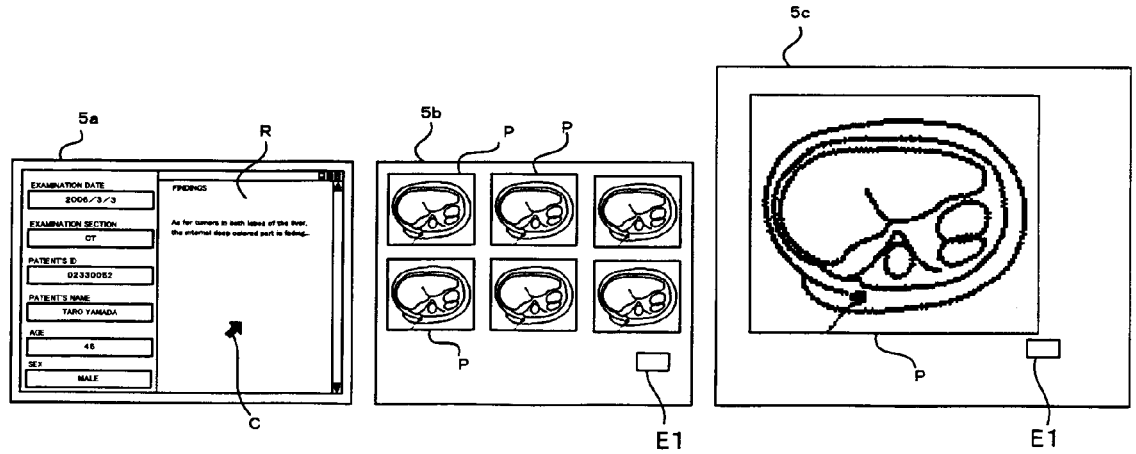
FIG. 27A shows a state in which a jump area is being displayed.

The FIG. 27A shows a state in which an entry jump area is being displayed. As shown in FIG. 27A, in a spot indicated in the entry jump area information on the display screen, the jump areas E1 and E1 are displayed. In case where a plurality of entry jump area information is preliminarily stored, the entire jump areas E1 and E1 are displayed, however, both are exclusively for an entry.

By using the pointing device 6 or the keyboard 7, when a region on the display screen is designated (83, Yes), the arithmetic control part 2 generates exit jump area information regarding the designated region as an exit jump area to be displayed (S84).

Figure 27B:
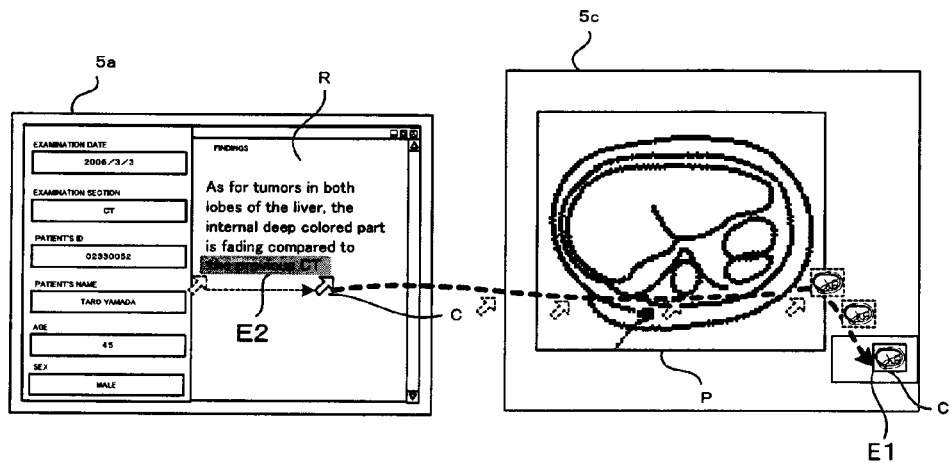
FIG. 27B shows a state in which a medical image has been subjected to a drag operation to enter a jump area that has been displayed after an exit jump area has been generated as a result of a region's designation.

As shown in FIG. 27B, for example, when a character string "previous CT" that has been entered in an interpretation report R is designated, the arithmetic control part 2 obtains coordinate range information on the designated region. Once the coordinate range of the designated region is obtained, the arithmetic control part 2 generates the exit jump area information, that is to be stored in the exit jump area information including the coordinate range information representing the obtained coordinate range. Moreover, the center coordinate of the coordinate range of the designated region is calculated and included in the exit jump area information as center coordinate information. That is, the character string such as "previous CT" that has been designated is later generated as the exit jump area E2 and is displayed on the display screen.

In a state in which the exit jump area has been set, as shown in FIG. 27B, by operating the pointing device 6, when display data such as medical image P is selected and while still in a drag-state if the mouse cursor C moves to the entry jump area E1 (S85, Yes), the arithmetic control part 2 reads out the center coordinate information from the exit jump area information (S86).

The arithmetic control part 2 regards the center coordinate information that has been read out as coordinate position data, and displays the mouse cursor C at the coordinate indicated in the coordinate position data while maintaining the drag-state (S87).

Figure 27C:
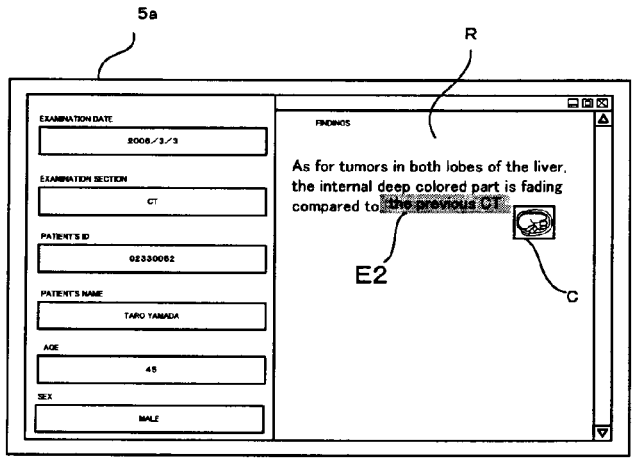
FIG. 27C shows a state in which the cursor has been jump-displayed from the entry jump area to the exit jump area while maintaining the drag-state.

FIG. 27C shows a state in which the mouse cursor has been jump-displayed from the entry jump area to the exit jump area while maintaining the drag operation. As shown in FIG. 27C, when the mouse cursor C moves to the jump area E1 while dragging the medical image P, the mouse cursor C is subjected to jump-display to the character string "previous CT" that has later become the exit jump area E2 as a result of region designation prior to the dragging while still dragging the medical image P.

According to the present modification example, due to the region designating operation, an exit jump area may be generated later in a desired place, and just by moving the mouse cursor C onto an entry jump area while dragging data such as a medical image P onto the exit jump area that has been generated in the desired place, the mouse cursor C may be jump-displayed while still in a drag-state. Due to this, particularly in the event of creating a link to a subject of linking that is to be determined later, the operation load of the pointing device 6 is reduced, thus preventing an operator's thought in creating an interpretation report from being destructed, and the enhancement in interpreting efficiency and the reduction of interpretation mistakes are achieved.

Figure 28:
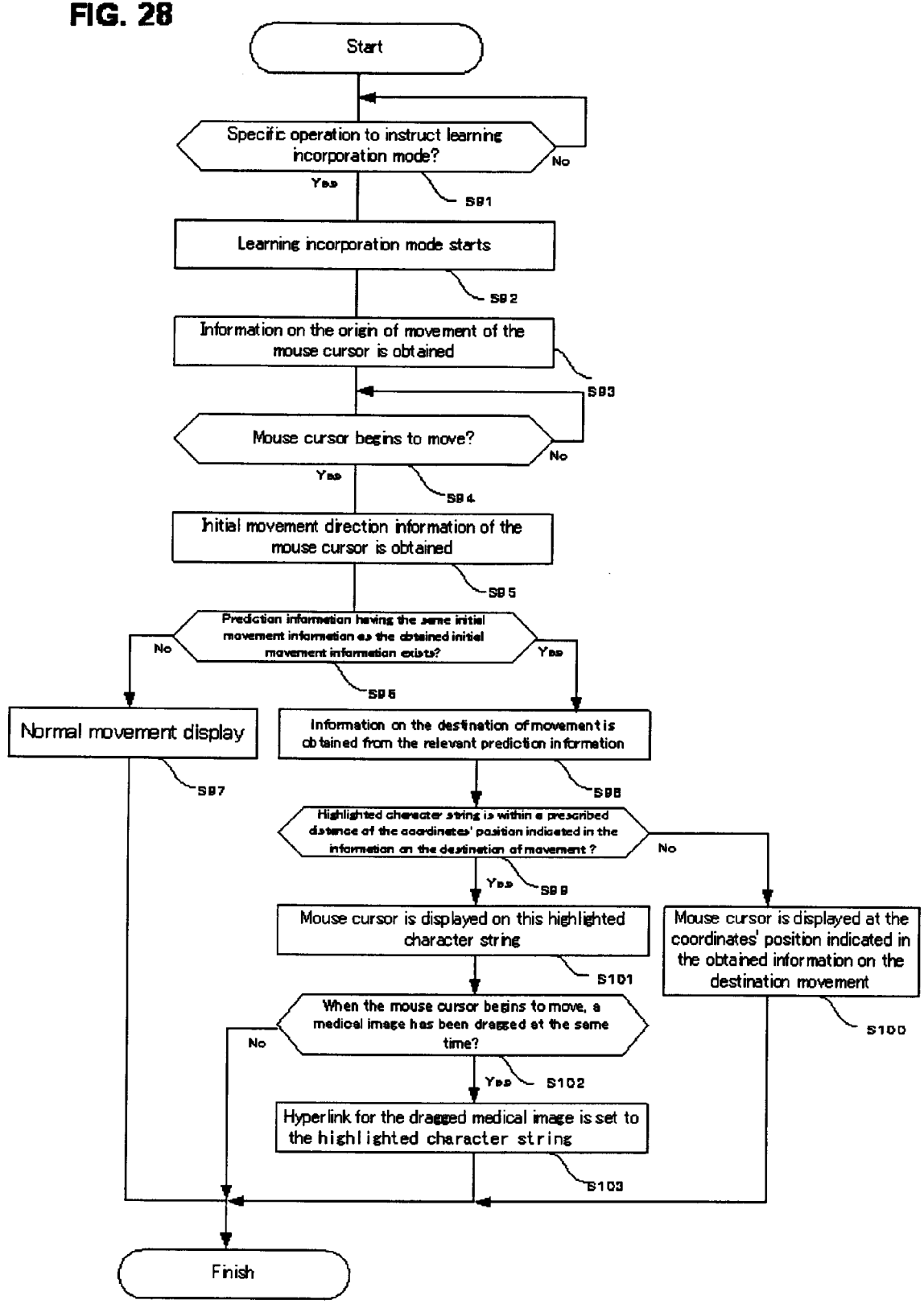
FIG. 28 shows the second modification example of predicted jump movement.

Moreover, a modification example of predicted jump movement conducted in the learning incorporation mode is further described in detail. FIG. 28 is a flow chart showing the processing of the predicted jump movement according to this modification example. In this modification example of the predicted jump movement, when an image or the like is preliminarily dragged to the origin of movement and a character string is present that is preliminarily highlighted within a prescribed range at the destination of movement according to information regarding the destination of movement, the mouse cursor C is moved to the position of the character string and a predetermined task for the character string, such as setting of a hyperlink, is performed.

First, if a specific operation to direct the learning incorporation mode such as pressing the F2 key is performed (S91, Yes), the learning incorporation mode is initiated (S92). The arithmetic control part 2 reads out a program in the learning incorporation mode from the external storage part 4 and rolls it out to the main storage part 3 for interpretation and execution. The learning incorporation mode continues, while the specific operation is being detected from the pointing device 6 or from the keyboard 7.

Once the learning incorporation mode begins, the arithmetic control part 2 obtains information regarding the origin of movement of the mouse cursor C (S93). Then, prompted by the operation of the pointing device 6, when the mouse cursor C begins to move (S94, Yes), the arithmetic control part 2 obtains directional information of initial movement of the mouse cursor C (S95).

Once information of the initial movement is obtained, the arithmetic control part 2 retrieves prediction information from the prediction information stored in the external storage part 4, having the same initial movement information as the initial movement information stored in the main storage part 3 (S96). In case of non-existence (S96, No), the mouse cursor C is subjected to normal movement (S97).

If the prediction information having the same initial movement information is present (S96, Yes), information regarding the destination of movement is obtained from the relevant prediction information (S98).

Once information regarding the destination of movement is obtained, the arithmetic control part 2 determines whether a highlighted character string is within a prescribed distance of the coordinates' position indicated in the information regarding the destination of movement (S99).

A character string is highlighted before this learning incorporation mode is directed, for example, before the F2 key or the like is pressed. By preliminarily using the pointing device 6 or the keyboard 7, when a region on the display screen is designated, the arithmetic control part 2 stores the designated region as information regarding the priority destination of movement in the main storage part 3. The arithmetic control part 2, when the information regarding the priority destination of movement is stored, determines whether the obtained information regarding the destination of movement and the center of the region indicated in the information regarding the priority destination of movement are within a prescribed distance. The prescribed distance has preliminarily been stored in the external storage part 4 as a part of program.

The arithmetic control part 2 calculates clearance between the coordinates indicated in the information regarding the destination of movement and the center coordinates of the region according to the information regarding the priority destination of movement from them. If the calculated value is smaller than the value according to the prescribed distance, it is determined that a highlighted character string is present within the prescribed distance of the coordinates' position indicated in the information regarding the destination of movement (S99, Yes). If the calculated value is greater than the value according to the prescribed distance, it is determined that a highlighted character string is not present within the prescribed distance of the coordinates' position indicated in the information regarding the destination of movement (S99, No).

When it is determined that a highlighted character string is not present within a prescribed distance of the coordinates' position indicated in the information regarding the destination of movement (S99, No), the mouse cursor C is displayed at the coordinates' position indicated in the information regarding the destination of movement that has been obtained (S100).

On the other hand, when it is determined that a highlighted character string is present within a prescribed distance of the coordinates' position indicated in the information regarding the destination of movement (S99, Yes), the mouse cursor C is displayed on this highlighted character string (S101). The arithmetic control part 2 calculates the center coordinates of the region indicated in the information regarding the priority destination of movement and displays the mouse cursor C at the center coordinates.

Moreover, when the mouse cursor C begins to move by operating the pointing device 6, the arithmetic control part 2 determines whether a medical image has been dragged at the same time (S102). If a medical image has not been dragged (S102, No), this predicted jump movement process is complete.

On the other hand, if it is determined that a medical image has been dragged (S102, Yes), the arithmetic control part 2 conducts predetermined task for the character string, such as setting of a hyperlink for the dragged medical image (S103), and then the predicted jump movement process is complete.

Figure 29A:
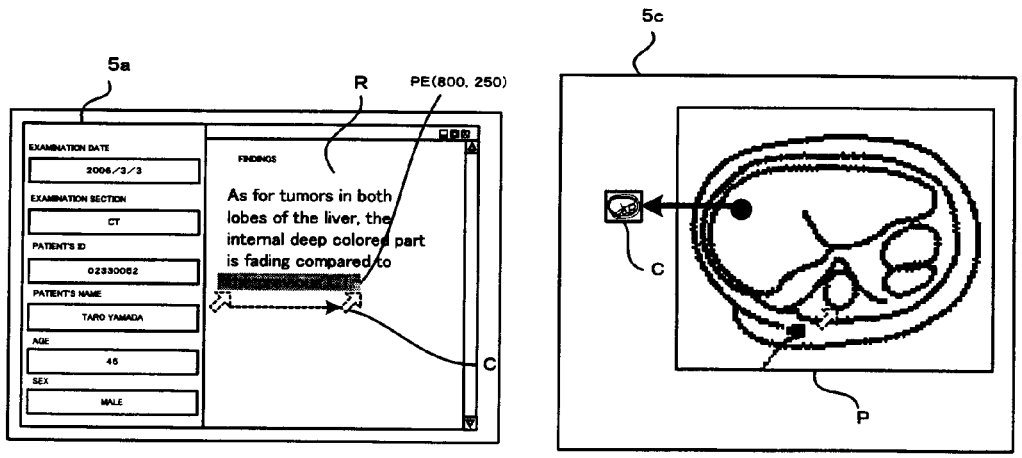
FIG. 29 shows a process of monitor displays related to the second modification example of predicted jump movement.

As shown in FIG. 29A, for example, when a character string "previous CT" that has been entered in an interpretation report R is selected, the fact that the selection has been made is visually acknowledged by changing the basic color of the character string to gray, for example. Then, the range of the character string is stored as information regarding the priority destination of movement PE. The center coordinates of the range according to this information regarding the priority destination of movement PE may, for example, be (800, 250).

Moreover, for example, when a medical image P is dragged in the prescribed direction by moving the mouse cursor C onto the medical image P, the predicted jump movement process related to the embodiment is performed in response to being prompted by this initial movement.

FIG. 30 is a pattern diagram showing the data structure of prediction information related to this embodiment. The prediction information is associated with prescribed distance information D representing a prescribed distance and a processing program. The processing program may, for example, be a hyperlink process. The prescribed distance information D may, for example, be for 100 pixels. This prescribed program is associated by storing even the process on character strings that have been highlighted by using the learning mode or the like.

Figure 29B:
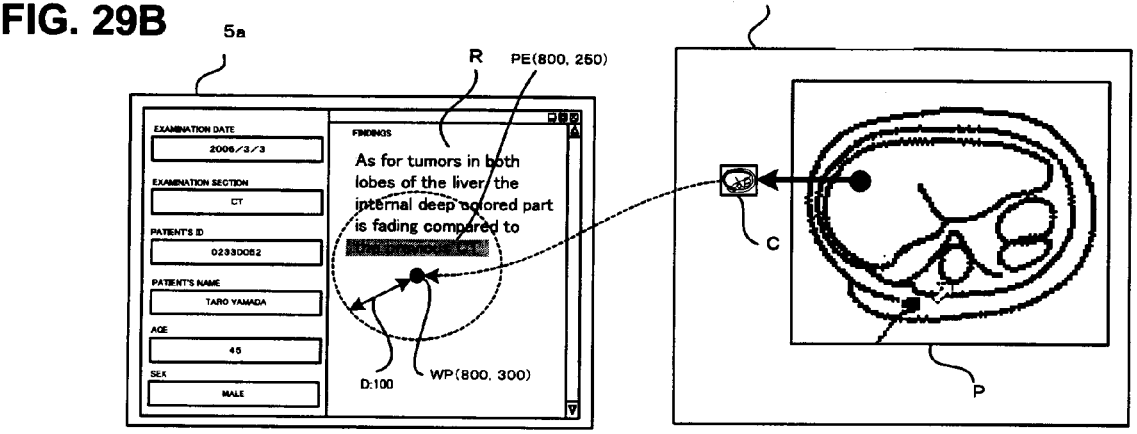

As shown in FIG. 29B, once the medical image P is dragged in the prescribed direction, the destination of movement is tentatively determined with reference to prediction information using the region of the origin of movement and the initial movement direction. The tentative destination of movement is the coordinates of the destination of movement according to information indicated by the destination of movement WP that is associated with information regarding the origin of movement in the prediction information. The coordinates according to the information regarding the destination of movement WP may, for example, be (800, 250).

Once the destination of movement is tentatively determined, the distance between the coordinates of this tentative destination of movement (800, 300) and the center coordinates of the highlighted character string (800, 250) is calculated. Then, the prescribed distance information D is read out from the prediction information and compared to the calculated distance. When the tentative destination of movement is (800, 300) and the center coordinate of the highlighted character string is (800, 250), the calculated distance is "50" and the prediction information is associated with the prescribed distance information D representing "100." In this case, as a result of comparison, it is determined that a highlighted character string is present within a prescribed distance of the coordinates' position indicated in the information regarding the destination of movement.

When it is determined that a highlighted character string is present within a prescribed distance of the coordinates' position indicated in the information regarding the destination of movement and the medial image P is being dragged during initial movement of the mouse cursor C, a prescribed program associated with the prediction information is read out, and the prescribed program is executed on the "previous CT," which is a highlighted character string.

Figure 29C:
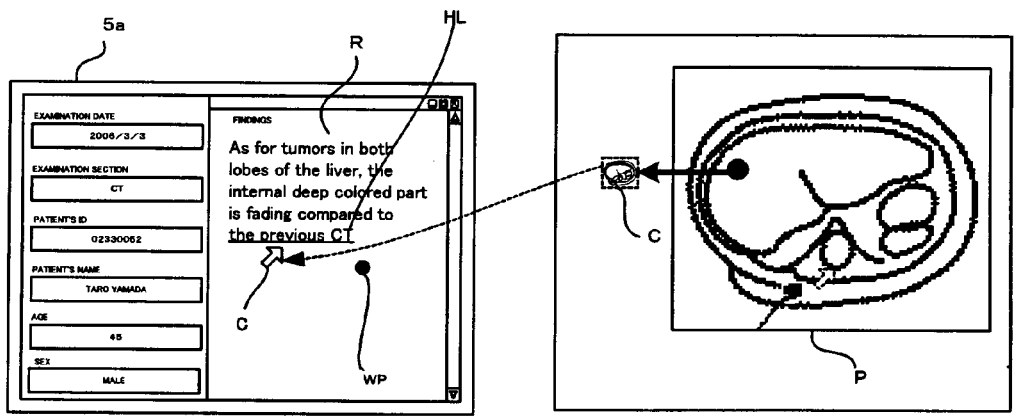

For example, as shown in FIG. 29C, when a hyperlink process is associated with a prescribed program, a hyperlink HL of a medical image C is set on the "previous CT," which is a highlighted character string. Then, the color of this "previous CT" changes, for example, to blue, and underlining is drawn to distinctively display that the hyperlink HL has been set. Moreover, the mouse cursor C is jump-displayed on the character string of this "previous CT." Furthermore, the display position of the mouse cursor may be moved onto the highlighted character string as in this modification example, or it may be moved to the destination of movement according to the information regarding the destination of movement.

According to the present modification, when subsequent processes can be predicted via highlighting or the like, it is possible also to create a link to this range simply by moving the mouse cursor C toward the range, and the operation of the pointing device 6 within that range may be omitted. Therefore, the operation load of the pointing device 6 is reduced, thereby preventing an operator's thoughts while drafting an interpretation report from being lost, and enhancement of interpreting efficiency as well as reduction of interpretation mistakes are thus achieved.

What is claimed is:

1. A medical image interpreting apparatus for supporting interpretation of medical images and creation of an interpretation report, comprising:
    a pointing device configured to move a cursor;
    a display part configured to display said medical images, said interpretation report, said cursor, and at least a set of areas on at least one display screen, said medical images being separate from said interpretation report;
    a button corresponding to each of said set of areas, each button corresponding to one of the medical images and the interpretation report, respectively;
    a determining part configured to determine movement of said cursor with respect to one of said areas; and
    a cursor moving part configured to move said cursor onto an other of said set of areas, when said determining part determines that said cursor has moved onto one of said set of areas, wherein
    said cursor moving part is configured to move said cursor onto said other of said set of areas corresponding to a pressed button, when said determining part determines that said cursor has moved onto one of said areas and any one of said buttons has been pressed.

2. A medical image interpreting apparatus according to claim 1, further comprising:
    an area generating part configured to preliminarily cause said display part to display one of said set of areas among said set of areas, and configured to cause said display part to display a designated region as the other of said set of areas, when the designated region is designated on said display screen, wherein
    said determining part determines whether said cursor has made a drag-movement to one of said set of areas while maintaining a drag-state of said medical image, and
    said cursor moving part moves said cursor onto the other of said set of areas while maintaining said drag-state, when said determining part determines that said drag-movement has been made.

3. A medical image interpreting apparatus according to claim 1, wherein the display part includes a plurality of monitors that each display one of the medical images and the interpretation report, and each of the plurality of monitors displays one of the areas.

4. A cursor-moving method of a medical image interpreting apparatus that has a pointing device for moving a cursor and supports the interpretation of a medical image and the creation of an interpretation report, comprising:
  displaying said medical image, said interpretation report, said cursor, and a set of areas on at least one display screen, said medical images being separate from said interpretation report,
  determining movement of said cursor with respect to said set of areas, and
  moving said cursor onto an other of said set of areas, when it is determined that said cursor has moved onto one of said set of areas, wherein
  said medical image interpreting apparatus further comprises a plurality of input buttons, each input button being preliminarily associated with one of said set of areas and each of the plurality of input buttons corresponding to one of the medical images and the interpretation report, respectively, and
  moving said cursor onto an area of said set of areas corresponding to a pressed button, when it is determined that said cursor has moved onto one of said set of areas and any one of said buttons has been pressed.

5. A cursor-moving method according to claim 4, further comprising:
  displaying one of said set of areas preliminarily,
  displaying a designated region as the other of said set of areas, when the designated region is designated on said display screen,
  determining whether said cursor has made a drag-movement to one of said set of areas while maintaining a drag-state of said medical image, and
  moving said cursor onto the other of said set of areas while maintaining said drag-state, when determined that said drag-movement has been made.

* * * * *

UNITED STATES PATENT AND TRADEMARK OFFICE
CERTIFICATE OF CORRECTION

PATENT NO. : 8,188,971 B2  
APPLICATION NO. : 11/685895  
DATED : May 29, 2012  
INVENTOR(S) : Jun Kawakami et al.

It is certified that error appears in the above-identified patent and that said Letters Patent is hereby corrected as shown below:

On the title page, Item (73), the Assignee's name is incorrect. Item (73) should read:

--(73) Assignees: Kabushiki Kaisha Toshiba, Tokyo (JP);  
Toshiba Medical Systems Corporation, Otawara-shi (JP)--

Signed and Sealed this  
Twenty-fourth Day of July, 2012

David J. Kappos  
*Director of the United States Patent and Trademark Office*